United States Patent [19]
Armstrong, III et al.

[11] Patent Number: 5,977,371
[45] Date of Patent: Nov. 2, 1999

[54] TANDEM ASYMMETRIC TRANSFORMATION PROCESS

[75] Inventors: Joseph D. Armstrong, III, Fanwood; J. Christopher McWilliams, Basking Ridge, both of N.J.

[73] Assignee: Merck & Co., Inc., Rahway, N.J.

[21] Appl. No.: 08/967,127

[22] Filed: Nov. 12, 1997

Related U.S. Application Data

[60] Provisional application No. 60/031,654, Nov. 19, 1996.
[51] Int. Cl.$^6$ .............................. C07F 3/06; C07C 233/00; C07C 235/00
[52] U.S. Cl. .......................... 548/101; 548/108; 549/212; 556/122; 556/135; 564/165; 564/191; 564/197
[58] Field of Search ..................................... 556/122, 135; 548/101, 108; 549/212; 564/165, 191, 197

[56] References Cited

U.S. PATENT DOCUMENTS

| | | | |
|---|---|---|---|
| 5,587,514 | 12/1996 | Liotta et al. | 564/134 |
| 5,643,878 | 7/1997 | Bold et al. | 514/19 |
| 5,663,168 | 9/1997 | Rosel et al. | 514/227.5 |
| 5,703,092 | 12/1997 | Xue et al. | 514/303 |

*Primary Examiner*—Porfirio Nazario-Gonzalez
*Attorney, Agent, or Firm*—Carol S. Quagliato; Melvin Winokur

[57] ABSTRACT

The instant invention provides a homologation process for making a zincate homoenolate from a carbon bound enolate zincate, by treating the carbon bound enolate zincate with an alkoxy lithium reagent. The homologation step can be coupled with a homoaldol reaction, as well as with other transmetallation reactions, in a one pot process. The zincate homoenolate is a useful intermediate in the preparation of a variety of different end-products, such as HIV protease inhibitors and renin inhibitors.

25 Claims, No Drawings

TANDEM ASYMMETRIC TRANSFORMATION PROCESS

This application claims the benefit of provisional application no. 60/031,654, filed Nov. 19, 1996.

BACKGROUND OF THE INVENTION

The preparation of organic compounds of high optical purity is becoming an increasingly important objective. To this end, numerous examples of methods involving chiral catalysts (both natural and unnatural) and covalently-bonded chiral auxiliaries can be cited. See for example, Noyori, R., *Asymmetric Catalysis in Organic Synthesis;* (John Wiley & Sons, Inc., New York) 1994; and Wong, C.-H., Whitesides, G. M., *Enzymes in Synthetic Organic Chemistry;* Tetrahedron Organic Chemistry Series, (Pergamon Press, Tarrytown, N.Y.) 1994; Vol. 12. Although often highly stereoselective, these methods typically embrace a single event in which bond-forming or bond-breaking takes place on a given substrate. For molecules with multiple stereocenters it would be desirable to couple several distinct asymmetric transformations in a single-vessel reaction sequence.

The reaction of the titanium homoenolate derived from 3 with N-tert-Boc-phenylalaninal 6 is known to yield the homoaldol product 4a as a single isomer as shown in Scheme 1. See, for example, (a) Armstrong III, J. D.; Hartner, Jr., F. W.; DeCamp, A. E.; Volante, R. P.; Shinkai, I. *Tetrahedron Lett.* 1992, 33, 6599; (b) DeCamp, A. E.; Kawaguchi, A. T.; Volante, R. P.; Shinkai, I. *Tetrahedron Lett.* 1991, 32, 1867; (c) Reetz, M. R.; Karin, R.; Griebenow, N. *Tetrahedron Lett.* 1994, 35, 1969; (d) Reetz, T. R.; Fox, D.N.A.; *Tetrahedron Lett.* 1993, 34, 1119; (e) Reetz, M. R. *Angew. Chem. Int. Ed. Engl.* 1991, 30, 1531; and (f) Kano, S.; Yokomatsu, T.; Shibuya, S. *Tetrahedron Lett.* 1991, 32, 233. The overall conversion of 1 to 4a by the known route requires four individual steps, including two stereodefining steps. The known route could likewise be used to produce 5a from 2.

Streamlining of the overall transformation of 1 to 4a would be desirable for improved time and cost efficiency. The success of such a process would require two distinct asymmetric transformations, an asymmetric homologation and an asymmetric homoaldol. The present invention addresses this problem by providing just such a tandem asymmetric process, which couples a 1,2-migration with a homoaldol reaction in a single-vessel reaction sequence. The process and intermediates described herein can be used in a wide variety of synthetic applications, and particularly this process can be used to make HIV protease inhibitors and endothelian antagonists.

SUMMARY OF THE INVENTION

One object of the instant invention is to provide a process for making a zincate homoenolate from the carbon bound enolate zincate IV,

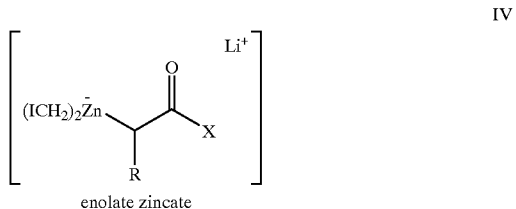

enolate zincate by treating IV with a suitable alkoxy lithium reagent, wherein R can be a variety of different substituent groups such as substituted and unsubstituted alkyl, alkenyl, aryl, heterocycle, amino, etc., and X is a di-substituted amino group which is capable of forming an N,N-disubstituted amide with the carbonyl group to which it is attached. The zincate homoenolate product produced by treatment of IV with an alkoxy lithium reagent is a versatile intermediate that can be coupled in situ with other reactions. Without intending to be bound by any particular two-dimensional drawing of the zincate homoenolate used herein, the zincate homoenolate product is depicted herein as formula VI for the sake of convenience. Accordingly, this homologation step can be illustrated below as Scheme 2.

SCHEME 1

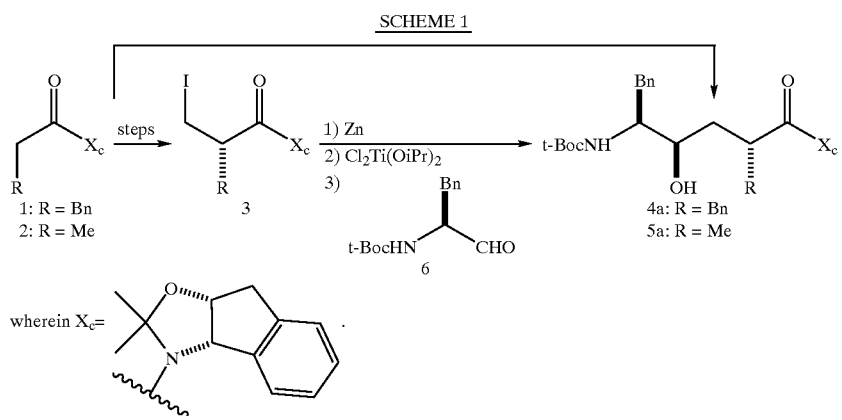

SCHEME 2

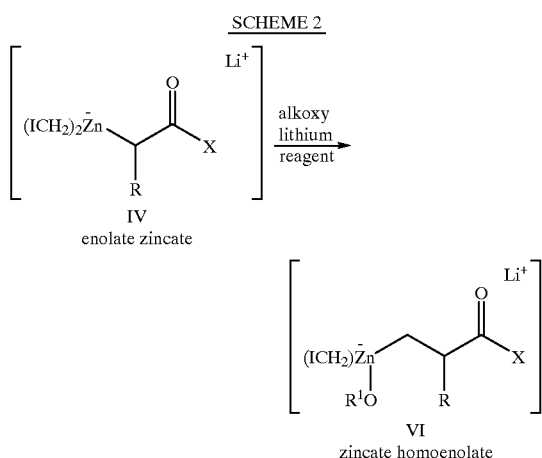
IV
enolate zincate

VI
zincate homoenolate

One particular emodirment of this object is to provide a process for making a chiral zincate homoenolate from the chiral carbon bound enolate zincate IV-i,

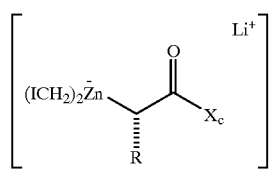
IV-i by treating IV-i with a suitable alkoxy lithium reagent, wherein Xc is a chiral auxiliary.

A second object of the instant invention is to provide a process for making the enolate zincate IV. A third object of the instant invention is to provide a one-pot process which couples the homologation step with a transmetallation and a homoaldol reaction in order to produce compounds of formula VII:

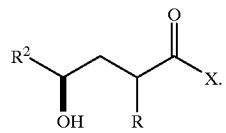
VII

In one embodiment, X is a chiral auxiliary (denoted as Xc) which will provide the chiral product VII-i:

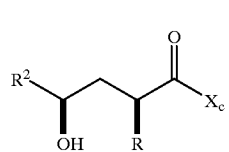
VII-i

Compounds of formula VII-i can further be converted to a variety of optically pure γ-lactones of formula VIII-i:

VIII-i

A fourth object of the instant invention is to couple the homologation reaction with additional transmetallation reactions to produce a greater variety of products with high optical purity. A fifth object is to describe intermediates which are useful for practicing the instant process. Additional objects will be evident from the following detailed description.

DETAILED DESCRIPTION OF THE INVENTION

One embodiment of the instant invention is outlined below in Scheme 3, which depicts the sequence of reactions starting with amide I and ending with the production of compounds of formula VII.

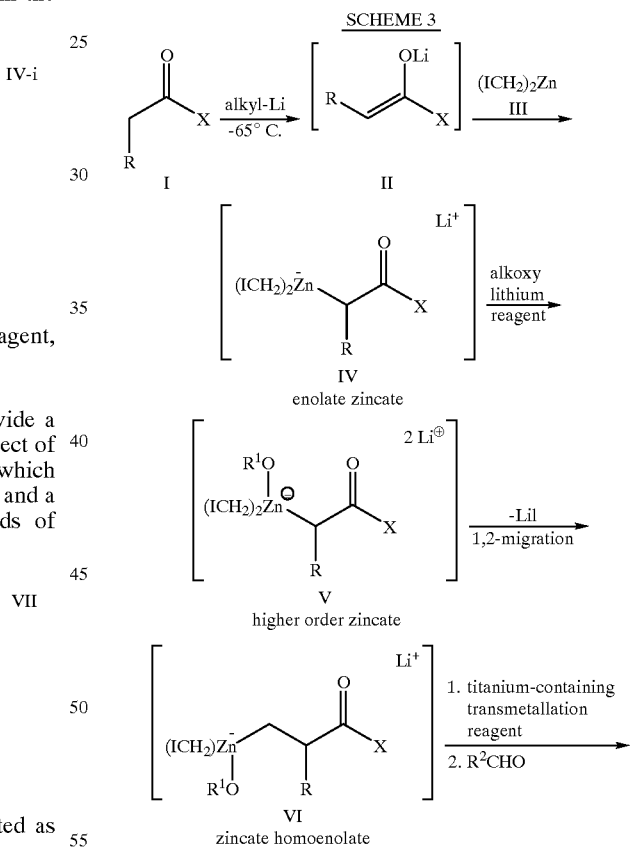

wherein
R can be any moiety capable of bonding to the alpha-carbon; for example R can be selected from but is not limited to the following groups each of which may be unsubstituted or substituted: —$C_{1-10}$ alkyl, phenyl, benzyl, heterocycle, —$C_{1-10}$ alkenyl including for example allyl, —$C_{1-10}$ alkyl-O—$C_{1-10}$ alkyl, —$C_{1-10}$ alkoxy, and a primary, secondary or tertiary amino such as —$NR^3R^4$ wherein each of $R^3$ and $R^4$ are independently selected from —H, —$C_{1-10}$ alkyl, phenyl, benzyl, —$C_{1-10}$ alkenyl and heterocycle;

alkoxy lithium reagent can be any alkyl-OLi, benzyl-OLi or lithium dialkoxide reagent, and the $R^1$—O— group in structures V and VI is the alkoxy derived from the alkoxy lithium reagent; for example, the alkoxy lithium reagent can be represented by the formulas $R^1$—OLi and $R^1(OLi)_2$ (for the dialkoxide), wherein $R^1$ can be selected from but is not limited to the following groups: —$C_{1-10}$ alkyl, —$C_{1-10}$ alkenyl, phenyl, benzyl and heterocycle;

$R^2CHO$ is an aldehyde, including alpha amino aldehydes derived from amino acids, including but not limited to the following examples:

N-t-butoxylcarbonyl-L-phenylalaninal,
N-t-butoxylcarbonyl-L-alaninal,
N-t-butoxylcarbonyl-L-leucinal,
N-t-butoxylcarbonyl-O-benzyl-L-tyrosinal,
N-t-butoxylcarbonyl-O-methyl-L-tyrosinal,
N-t-butoxylcarbonyl-L-valinal, and
t-butyl (S)-4-formyl-2,2-dimethyl-3-oxazolidinecarboxylate all of which are commercially available;

for example, $R^2$ can be selected from —$C_{1-10}$ alkyl, —$C_{1-10}$ alkenyl, phenyl, benzyl, heterocycle,

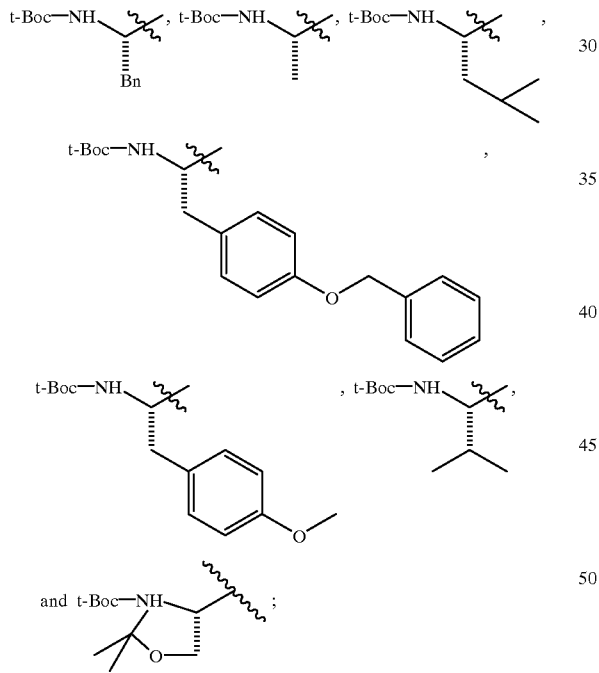

and X is a di-substituted amino group which is capable of forming an N,N-disubstituted amide with the carbonyl group to which it is attached; for example X can be —$NR^7R^8$ which forms an N,N-disubstituted amide with the carbonyl group to which it is attached, as illustrated in the bracketed part of formula VII as follows:

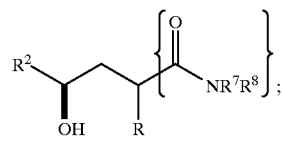

any stable N,N-disubstituted amino group, that is, wherein both $R^7$ and $R^8$ are not —H, can be employed, for example a) $R^7$ and $R^8$ can be independently selected from —$C_{1-10}$ alkyl, —$C_{1-10}$ alkyl-O—$C_{1-10}$ alkyl, —$C_{2-10}$ alkyl-$C_{1-10}$ alkenyl, phenyl, benzyl, heterocycle, and —C(O)O—$R^9$, and wherein $R^9$ is selected from —$C_{1-10}$ alkyl, —$C_{1-10}$ alkyl-O—$C_{1-10}$ alkyl, —$C_{1-10}$ alkyl-$C_{1-10}$ alkenyl, phenyl, benzyl, and heterocycle;

b) $R^7$ and $R^8$ together can be —$(CH_2)_n$— wherein n is an integer selected form 2 to 5, so that $R^7$ and $R^8$ are joined together with the nitrogen to which they are attached to form cyclic structure of formula

c) $R^7$ and $R^8$ together with the nitrogen to which they are attached can be joined to form an oxazolidinone of formula

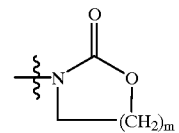

wherein m is an integer selected from 1 and 2, and d) $R^7$ and $R^8$ together with the nitrogen to which they are attached can form a chiral auxiliary, denoted as Xc, for example
 i) Aminoindanol-based auxiliaries such as:

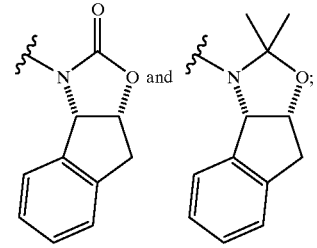

ii) Oxazolidinones and their derivatives such as:

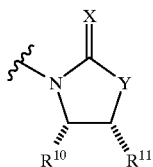

wherein

X is selected from O and S,

Y is selected from O, —N($C_{1-10}$alkyl)—, and S, $R^{10}$ is selected from —$C_{1-10}$alkyl, —C(O)$C_{1-10}$ alkyl, benzyl, —COO$C_{1-10}$ alkyl, and aryl (e.g., i-Pr, t-Bu, Bn, Ph, $CO_2$Et), and $R^{11}$ is selected from —$C_{1-10}$alkyl and aryl (e.g. Me, Ph);

iii) $C_2$ Symmetric Diamines such as:

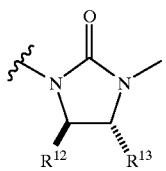

wherein $R^{12}$ and $R^{13}$ are both the same and are selected from $C_{1-10}$ alkyl and aryl, or $R^{12}$ and $R^{13}$ are joined together as an alkyl chain such as —($CH_2$)$_4$—;

iv) Meyer's Auxiliaries, such as:

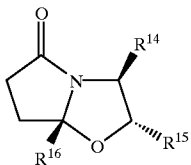

wherein $R^{14}$ is $C_{1-10}$ alkyl (e.g. iPr, $CH_2OH$), $R^{15}$ is aryl (e.g. Ph), and $R^{16}$ is selected from $C_{1-10}$ alkyl and H (e.g. Me);

v) $C_2$ Symmetric Amides, such as:

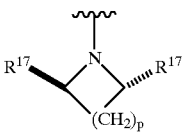

wherein $R^{17}$ is an alkyl ether such as —$C_{1-10}$ alkyl-O—$C_{1-10}$ alkyl, —$C_{1-5}$ alkyl-O—$C_{1-5}$ alkyl-O—$C_{1-5}$ alkyl, and —$C_{1-10}$ alkyl-O-Si($C_{1-5}$ alkyl)$_3$ (e.g., —$CH_2OCH_2OCH_3$ —$CH_2OBn$, or —$CH_2OSi$(alkyl)$_3$), and p is an integer selected from 0, 2, and 3;

vi) Camphor Derivatives, such as:

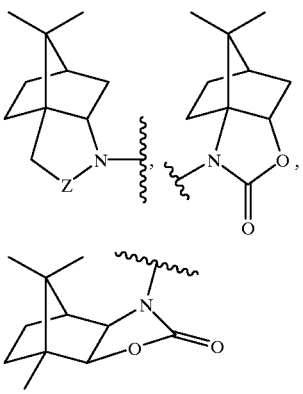

wherein Z is selected from O and $SO_2$; and vii) Miscellaneous Derivatives such as:

a)

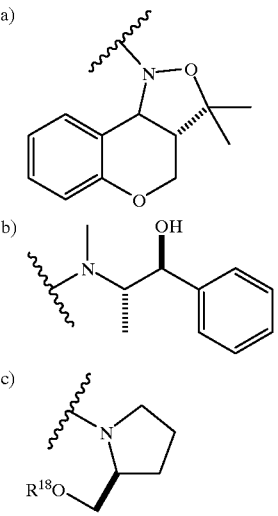

b)

c)

wherein $R^{18}$ is selected from H, $C_{1-10}$ alkyl, and silyl, and

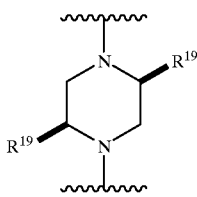

wherein $R^{19}$ is $C_{1-10}$ alkyl (e.g., Bn, i-Pr).

Xc is preferably

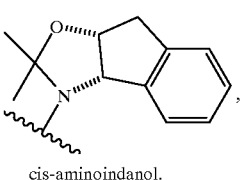

cis-aminoindanol.

The reactions in Scheme 3 are run in a single vessel under an inert atmosphere, such as nitrogen or argon, using an aprotic solvent or mixtures thereof, at low temperatures in the range of about −50° C. to −80° C. It is to be noted, however, that when X is an oxazolidinone, the acceptable temperature range for the reaction is much broader, for example it can range from −80° C. up to room temperature. Examples of suitable aprotic solvents include tetrahydrofuran (THF), dimethoxyethane (DME), toluene, di-ethyl ether, methyl-t-butyl ether (MTBE), and the like.

The lithium enolate II is formed by treating I with at least one equivalent of a suitable alkyl lithium reagent, many of which are commonly known in the art. Examples include n-BuLi, t-BuLi, s-BuLi and PhLi, with n-BuLi being preferred. This step is preferably performed at a temperature of $\leq -65°$ C. The reaction is stirred until the lithium enolate II is formed (generally about 10 to 30 minutes is sufficient). The lithium enolate II is then added to a solution of at least 0.5 equivalents of bis(iodomethyl)zinc III in an aprotic solvent such as THF at a temperature of $\leq -70°$ C., which generates a solution of the enolate zincate IV. Low temperatures and inverse addition of II to III are necessary to minimize formation of sideproduct.

Homologation of the enolate zincate IV is achieved by treating IV with 1 to 4 equivalents, preferably 3 equivalents, of an alkoxy lithium reagent. The term "alkoxy lithium reagent" is intended to include any alkyl-OLi, benzyl-OLi or lithium dialkoxide reagent. The group $R^1$—O— in structures V, VI, V-i and VI-i is derived from the alkoxy portion of the alkyl-OLi or benzyl-OLi reagent that is used; for example, if benzyl-OLi is used, $R^1$—O— represents the benzyl-O— group. When a lithium dialkoxide is used, $R^1$—O will represent the LiO-alkoxy portion of the lithium dialkoxide; for example, if the lithium dialkoxide

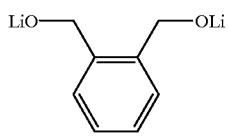

is used, then $R^1$—O— represents

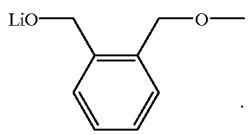

Representative formulas used herein for alkoxy lithium reagents are $R^1$—OLi and $R^1(OLi)_2$. Representative examples of suitable alkoxy lithium reagents include but are not limited to ethyl-OLi, n-propyl-OLi, lithium benzylalkoxide (BnOLi), LiO(CH$_2$)$_2$OLi and LiO(CH$_2$)$_3$OLi; preferably, BnOLi is used at a temperature of $\leq -70°$ C., to produce the zincate homoenolate VI. Without intending to be bound by any one mechanistic theory, it is hypothesized that the homologation to the zincate homoenolate VI proceeds through the higher order zincate V, which undergoes a 1,2 migration to form VI.

Via a transmetallation step, the homologation procedure can be coupled to other reactions. For example as shown in Scheme 3, hydroxyethylene dipeptide isosteres (which are intermediates in the production of HIV protease inhibitors and renin inhibitors) of formula VII can be prepared from VI using a titanium transmetallation reagent. Transmetallation of the zincate homoenolate VI to form a titanium homoenolate intermediate is effected by treating VI with at least one equivalent of a titanium reagent selected from Cl$_3$Ti(O-isopropyl), TiCl(O-isopropyl)$_3$, TiCl$_2$(O-isopropyl)$_2$, and TiCl$_4$; preferably Cl$_3$Ti(O-isopropyl) is employed. The titanium transmetallation reagent is added to VI at a sufficiently low temperature, preferably at least −80° C.; once the addition is complete, the reaction is allowed to warm, preferably to $\leq -20°$ C. and most preferably to about −20° C., and it is maintained at that temperature until it is used. While maintaining the temperature, the aldehyde $R^2$CHO is next added to the titanium homoenolate to form the hydroxyethylene dipeptide isostere VII.

The symbol "X" is intended to encompass di-substituted amino groups which are capable of forming an N,N-disubstituted amide with the carbonyl to which X is attached as described above; di-substituted amino groups which are chiral auxiliaries and those which are not are both included within the scope of this invention. However, a further embodiment of the process described in Scheme 3 involves the practice of the process where X is a chiral auxiliary, and is summarized below in Scheme 4. The symbol "Xc" is used herein to denote where X is intended to be a chiral auxiliary.

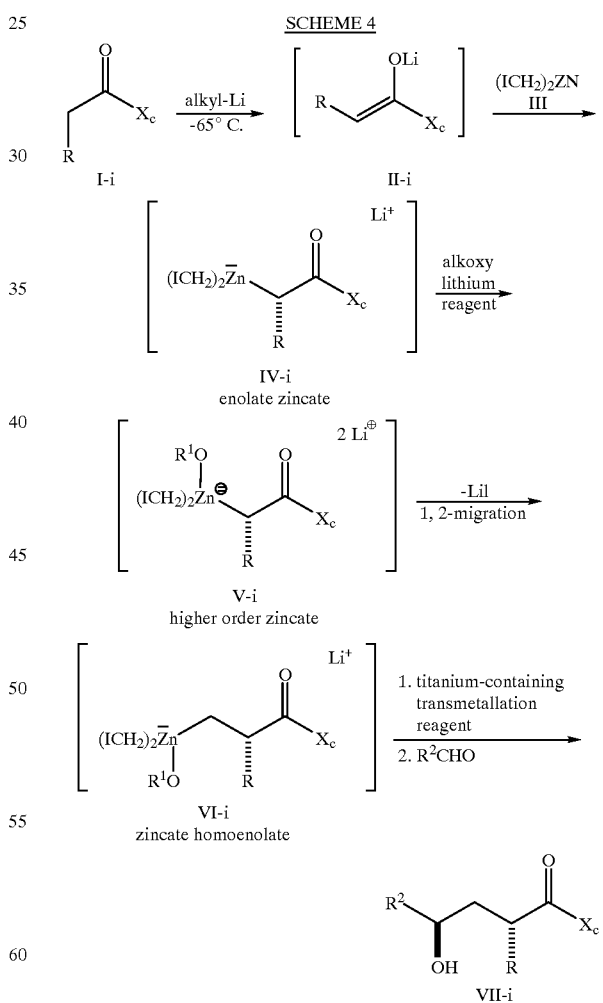

Any of the chiral auxiliaries which are commonly known in the art can be used with the instant process. A chiral auxiliary as used herein and as understood in the art is a di-substituted amino group which is put into a molecule to set a stereocenter in another part of that molecule. For example, the alpha carbon stereocenter in VII-i is set by use of the chiral auxiliary as shown in Scheme 4. After the desired stereocenter has been set, the chiral auxiliary may optionally be removed so that it is not part of the final product, or it may be maintained in the final product. An example of a product which retains its chiral auxiliary is the HIV protease inhibitor indinavir sulfate, marketed in the U.S. under the trademark CRIXIVAN®, and which has the following structure:

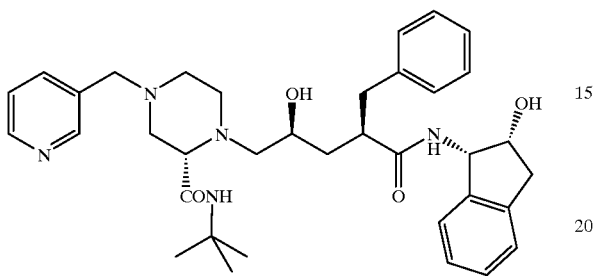

Although an acceptable enantiomeric excess (ee) will vary based on many factors, it is preferable that the chiral auxiliary used with the instant process result in a product of formula VII-i having high optical purity, for example at least 50% de.

Examples of Xc, i.e., chiral auxiliaries, include but are not limited to those described above, as well as those disclosed in the following publications:

Askin, D. et al. J. Org. Chem. 1992, 57, 2771;
Maligres, P. E. et al. Tetrahedron Lett.1995, 36, 2195;
Gosh, A. K. et al. J. Chem. Soc. Chem. Commun. 1992, 1673;
Y. Nagao et al. J. Am. Chem. Soc. 1988, 110, 289;
S. E. Drewes et al. Tetrahedron: Asymmetry1992, 3, 515;
Evans, D. A. et al. J. Org. Chem.1991, 56, 5750;
Evans, D. A. et al. Angew. Chem., Int. Ed. Engl.1987, 26, 1184;
Hsiao, C-N. et al. Tetrahedron Lett. 1985, 26, 4855;
Versteeg, M. et al. J. Chem. Soc., Chem. Commun.1995, 1317;
Huang, N. Z. et. al. Tetrahedron1990, 46, 8067;
Sankhavasi, W. et al. Bull. Chem. Soc. Jpn. 1991, 64, 1425;
Armstrong, R. W. et al. Tetrahedron Lett. 1991, 32, 5749;
Hanessian, S. et al. Synlett.1990, (9), 501;
Meyers, A. I. et al. Heterocyclies1990, 30, 339;
Meyers, A. I. et al. J. Org. Chem. 1990, 55, 791;
Meyers, A. I. et al. Tetrahedron1987, 43, 5663;
Meyers, A. I. et al. J. Am. Chem. Soc. 1984, 106, 1146;
Stafford, J. A. et al. J. Org. Chem.1990, 31, 2029;
Tanner, D. et al. Tetrahedron Lett. 1991, 32, 2533;
Nadji, S. et al. J. Org. Chem.1990, 55, 6241;
Yamaguchi, M. et al. Tetrahedron Lett.1986, 27, 959;
Katsuki, T. et al. Tetrahedron Lett. 1985, 26, 5807;
Oppolzer, W. et al. Tetrahedron Lett. 1993, 34, 4321;
Bonner, M. P. et al. J. Am. Chem. Soc. 1991, 113, 1299;
Yan, T-H. et al. Tetrahedron Lett.1991, 32, 4959;
Abiko, A. et al. Angew. Chem., Int. Ed. Engl. 1995, 34, 793;

Meyer, A. G. et al. J. Am. Chem. Soc.1994, 116, 9361;
White, J. D. et al. J. Org. Chem. 1990, 55, 5938;
Tomioka, et al. J. Chem. Soc., Perkin Trans 11990, 426; and
K. Soal et al. Bull. Chem. Soc. Jpn. 1987, 60, 3450; all of which are herein incorporated by reference. Xc is preferably

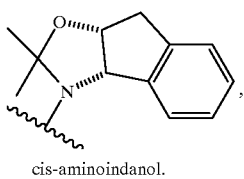

cis-aminoindanol.

The reaction procedures and conditions for Scheme 4 are the the same as those described above for Scheme 3. The difference is that by using a chiral auxiliary Xc, this embodiment of the invention successfully couples two distinct assymetric transformations in a single vessel reaction sequence: an asymmetric homologation and an asymmetric homoaldol reaction. The stereoselectivity of the homologation step to form the zincate homoenolate VI-i is excellent and the overall two-step transformation to VII-i likewise proceeds with excellent stereoselectivity.

A more specific example of the reaction sequence depicted in Scheme 4 is shown below in Scheme 5, wherein Xc is cis-aminoindanol. The numbers used to identify structures in Scheme 5 correspond to the numbers used in the Examples and in Tables I and 2. Several aldehydes were examined as homoaldol substrates in the transformation illustrated in Scheme 5, and the results are shown in Table 1.

The stereoselectivity of the homoaldol reaction was determined by transformation to the lactones (see below), and examination of coupling constants and nOe effects. The highest diastereoselectivity in the homoaldol reaction is observed for N-tert-Boc aldehydes derived from L-amino acids and the titanium homoenolate derived from 13a (entries A and C). Diastereoselectivity in the homoaldol reaction with aryl and aliphatic aldehydes decreased with decreasing steric bulk alpha to the aldehyde.

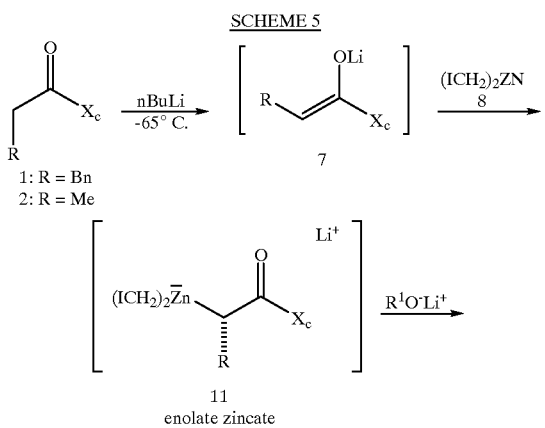

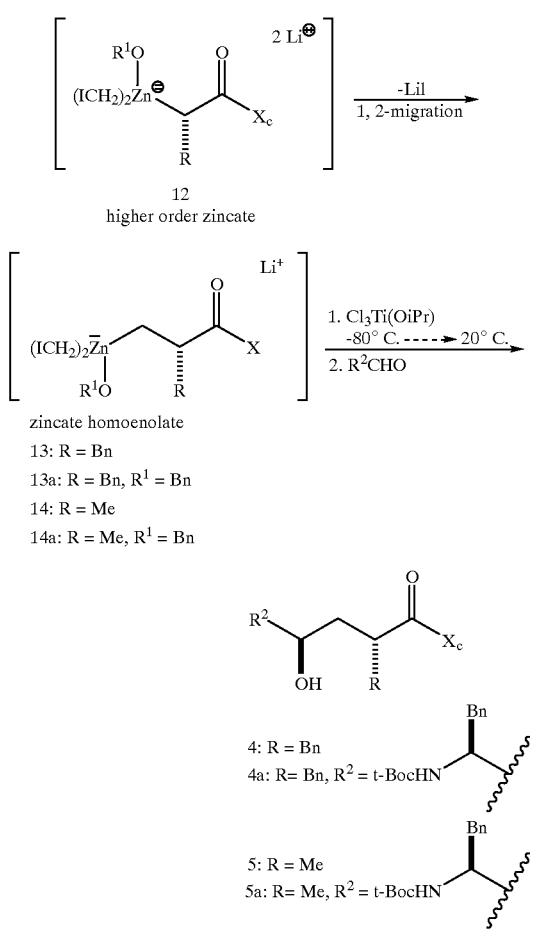

12
higher order zincate zincate homoenolate
13: R = Bn
13a: R = Bn, R¹ = Bn
14: R = Me
14a: R = Me, R¹ = Bn 4: R = Bn
4a: R= Bn, R² = t-BocHN-CH(Bn)-

5: R = Me
5a: R= Me, R² = t-BocHN-CH(Bn)-

TABLE 1

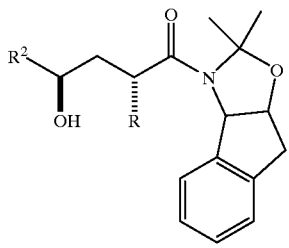

Tandem Asymmetric 1,2-Migration/Homoaldol Reactions[a]

| Entry | R² | R | Product | Temp. (° C.) | de (%)[b] |
|---|---|---|---|---|---|
| A | t-BocNH-CH(Bn)- | Bn | 4a | −20 | 99 |
| B | t-BocNH-CH(Bn)- | Me | 5a | −20 | 82 |

TABLE 1-continued

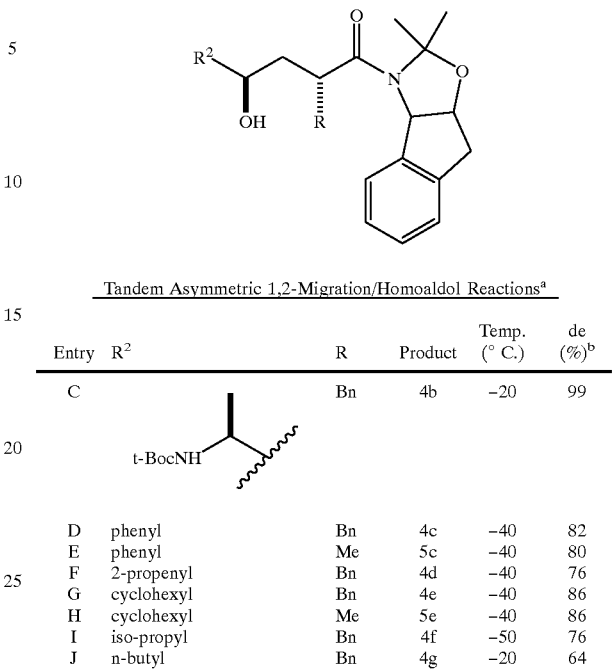

Tandem Asymmetric 1,2-Migration/Homoaldol Reactions[a]

| Entry | R² | R | Product | Temp. (° C.) | de (%)[b] |
|---|---|---|---|---|---|
| C | t-BocNH-CH- | Bn | 4b | −20 | 99 |
| D | phenyl | Bn | 4c | −40 | 82 |
| E | phenyl | Me | 5c | −40 | 80 |
| F | 2-propenyl | Bn | 4d | −40 | 76 |
| G | cyclohexyl | Bn | 4e | −40 | 86 |
| H | cyclohexyl | Me | 5e | −40 | 86 |
| I | iso-propyl | Bn | 4f | −50 | 76 |
| J | n-butyl | Bn | 4g | −20 | 64 |

[a]Reactions were run with 5 equivalents of aldehyde, except for entries A–C, in which 0.5 equivalents of the corresponding aldehydes was employed.
[b]Refers to stereoselectivity of homoaldol reaction as determined by GLC after silylation of the crude mixtures, or by HPLC.

Generally, the major isomers from the tandem 1,2-migration/homoaldol transformation were isolated in pure form by simple flash chromatography. Conditions for removal of the auxiliary are quite mild. Removal of the chiral auxiliary with formation of the cyclic chiral compounds of formula VIII-i is shown in Scheme 6. Compound VII-i can be treated with about 1 to 1.1 equivalents of p-toluenesulphonic acid monohydrate at a temperature in the range of 0° C. to 50° C. in an aromatic, ethereal or halogenated solvent, with toluene being preferred as solvent. The reaction need not be performed under an inert atmosphere, but an inert atmosphere is preferred.

SCHEME 6

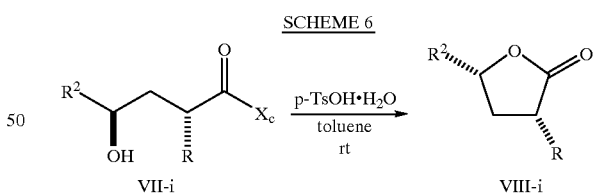

A more specific example of the reaction sequence depicted in Scheme 6 is shown below in Scheme 7, wherein R is benzyl and Xc is cis-aminoindanol. Treating representative γ-hydroxyamides 4 with p-toluenesulphonic acid monohydrate induces cyclization to the lactones 15 in good yield. Furthermore, the (1R, 2S)-cis-aminoindanol crystallizes from the toluene solution as the p-toluenesulfonate salt 16, and is recovered by simple filtration. Thus, this method provides access to a variety of optically pure, γ-lactones. Some specific examples of the reaction shown in Scheme 7 are presented in Table 2, wherein specific definitions for R² for the starting amide 4 and the resulting lactone 15 are listed.

SCHEME 7

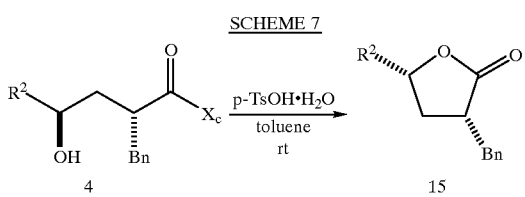

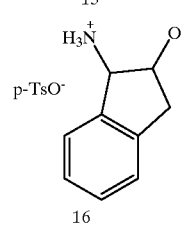

TABLE 2

Cyclization to γ-Lactones

| Entry | Amide | R² | Lactone |
|---|---|---|---|
| A | 4a | t-BocNH—CH(Bn)— | 15a |
| B | 4c | Ph | 15c |
| C | 4f | iso-propyl | 15f |

The zincate homoenolate VI can be coupled via transmetallation reactions in addition to the titanium based transmetallation reactions described above. Alkyl-, aryl- and acid-halides, and alkyl- and aryl-triflates can be coupled with VI via copper and palladium based transmetallations.

For example as shown in Scheme 8, a compound of structure VI-i can be coupled to an alkyl, aryl or acyl group by treating VI-i with 1 to 5 equivalents of $R^{20}$—Y in the presence of 0.01 to 0.1 equivalents of palladium based catalyst $(Ph_3P)_2PdCl_2$. The reaction can be done in an ethereal solvent, with THF being the preferred solvent, at a temperature in the range from 0° C. to 60° C., preferably under an inert atmosphere.

SCHEME 8

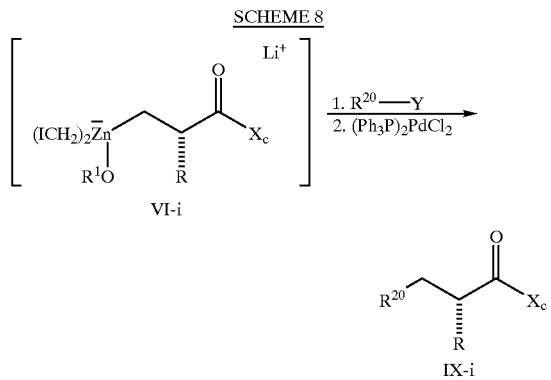

wherein $R^{20}$ is selected from $C_{1-10}$ alkyl, $C_{1-10}$ alkenyl, aryl and $C_{1-10}$ alkyl-C(O)—, and Y is selected from halo (I, Br, Cl) and —OSO₂CF₃ (abbreviated as —OTf), provided that when $R^{20}$ is $C_{1-10}$ alkyl-C(O)—, Y is halo.

Alternatively, CuCN can be employed as the transmetallation agent as shown in Scheme 9. A compound of formula VI-i can be treated with 0.1 to 1.1 equivalents of CuCN and from 1 to 5 equivalents of an alkyl halide of formula $R^{21}Y'$ to form X-i. The reaction is performed at a temperature in the range from −60° C. to room temperature, under an inert atmosphere in an ethereal solvent, preferably THF.

SCHEME 9

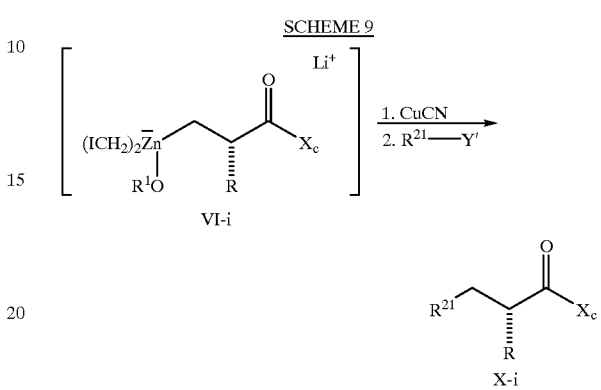

wherein $R^{21}$ is selected from $C_{1-10}$ alkyl and $C_{1-10}$ alkenyl, and Y' is halo (I, Br, Cl).

As used herein "alkyl" is intended to include both branched- and straight-chain saturated aliphatic hydrocarbon groups having the specified number of carbon atoms, e.g., methyl (Me), ethyl (Et), propyl, butyl (Bu), pentyl, hexyl, heptyl, octyl, nonyl, decyl and the isomers thereof such as isopropyl (i-Pr), isobutyl (i-Bu), secbutyl (s-Bu), tertbutyl (t-Bu), isopentyl, isohexyl and the like. The term "alkyl" includes both unsubstituted and substituted alkyl groups, for example mono-, di- and tri-substituted alkyl groups; one example is a benzyl group, wherein the aryl ring of the benzyl group may also be unsubstituted or substituted. "Alkoxy" represents an alkyl group having the indicated number of carbon atoms attached through an oxygen bridge, e.g., methoxy, ethoxy, propyloxy, iso-propoxy, n-butoxy, iso-butoxy, sec-butoxy, t-butoxy and the like, and as noted above may be either unsubstituted or substituted on the alkyl portion so as to inlcude, for example, benzyloxy. The specific term "alkoxy lithium reagent" is defined above in the specification. The term "alkenyl" is intended to include both branched- and straight-chain hydrocarbon groups having the specified number of carbon atoms with one or more carbon-carbon double bonds which may occur at any stable point along the chain, e.g., propenyl (allyl), butenyl, pentenyl, hexenyl, heptenyl, octenyl, nonenyl, decenyl, 3,4-dimethyl-1-pentenyl, 4-methyl-pent-2-enyl, and the like. The term "alkenyl" includes both unsubstituted and substituted alkenyl groups, for example mono-, di- and tri-substituted alkenyl groups. Included in this invention are all E,Z diastereomers.

The term halo or halogen is meant to include chloro, bromo and iodo, unless otherwise noted. The term "aryl" is meant to include phenyl and naphthyl. The term "aryl" includes both unsubstituted and substituted aryl groups, for example mono-, di- and tri-substituted aryl groups.

The terms "heterocycle" and "heterocyclic" are meant to include: (a) an unsubstituted or substituted five or six membered aromatic or saturated ring which consists of carbon atoms and from one to three heteroatoms selected from the group O, N, S, and NH, and (b) an unsubstituted or substituted eight to ten membered bicyclic ring system which is saturated or completely or partially unsaturated and which consists of carbon atoms and from one to three heteroatoms selected from the group O, N, S, and NH.

For example, the term "heterocycle" includes a five or six-membered heterocycle ring fused to a benzene, pyridine or pyrimidine ring. The term "heterocycle" includes both unsubstituted and substituted heterocyclic groups, for example mono-, di- and tri-substituted heterocyclic groups. Substituents can be bonded to any available carbon atoms or heteroatom in the ring which results in the creation of a stable structure. The heterocyclic ring may be attached within the generic structural formulae at any carbon atom or heteroatom, e.g., N, in the ring which results in the creation of a stable structure. Examples of heterocycle groups include pyrrolyl, triazolyl, pyrazolyl, imidazolyl, pyridinyl, pyrimidinyl, pyrazinyl, furanyl, pyranyl, thiophenyl, oxazolyl, thiazolyl, indolyl, benzimidazolyl, benzofuranyl, benzopyranyl, quinolyl, isoquinolyl and the like.

Substituents on the alkyl, alkoxy, alkenyl, aryl and heterocycle may be any substituents which form a stable structure when used with the instant process steps. Examples of such substituents include but are not limited to: $C_{1-10}$ alkyl, $C_{1-10}$ alkenyl, phenyl, —F, —Cl, —I, —Br, oxo, halo, amino, mono- and di-substituted amino, —$NO_2$, —CN, —$CF_3$, —$SO_2$—$C_{1-10}$ alkyl, and —C(O)$R^{22}$ wherein $R^{22}$ is selected from —$C_{1-10}$ alkyl, —$OC_{1-10}$ alkyl, and —$NR^3R^4$.

Abbreviations used throughout the application are as follows:

Ac is acetyl ($CH_3C(O)$—); t-Boc is N-t-butoxycarbonyl; THF is tetrahydrofuran; ee is enantiomeric excess; de is diasteriomeric excess; p-TsOH is para-toluenesulfonic acid;

Tf and triflate is —$SO_2CF_3$.

The compounds described herein are chiral and may occur as racemates, racemic mixtures and as individual diasteriomers with all such isomeric forms being included within the scope of this invention, except where the stereoconfiguration of a specific chiral center is defined or depicted otherwise.

EXAMPLES

All reagents were purchase from Aldrich accept N-tert-Boc-L-alaninal and N-tert-Boc-L-valaninal, which were purchase from Peninsula Laboratories, Inc. All reagents were used as received, accept benzaldehyde and methacrolein, which were distilled prior to use. N-tert-Boc-L-phenylalaninal was prepared by known procedures (see, for example Armstrong III, J. D.; Hartner, Jr., F. W.; DeCamp, A. E.; Volante, R. P.; Shinkai, I. *Tetrahedron Lett.* 1992, 33, 6599). Tetrahydrofuran (THF) and methylene chloride ($CH_2Cl_2$) were dried over 4 Å molecular sieves and degassed prior to use. All reactions were performed under a dry nitrogen atmosphere. $T_i$ refers to internal temperature.

GLC was performed on an Hewlett-Packard 5890, with Hewlett-Packard HP-5 (30 m×0.32 mm) or J & W Scientific DB-23 (30 m×0.32 mm) capillary columns. Complete silylation of crude mixtures prior to analysis was accomplished with Tri-Sil, purchased from Pierce. HPLC was performed on Hewlett-Packard 1050 or 1090 instruments, with Zorbax Rx-C8 or Zorbax SB-Phenyl reverse-phase columns. Thin-layer chromatography was performed on EM Science silica gel 60 plates with F-254 indicator (250 μm thickness). Visualization was accomplished by UV light or phosphomolybdic acid solution. Column chromatography was performed with EM Separations Technology Silica Gel 60 (0.040–0.063 μm particle size). FT-IR were recorded on a Nicolet Magna-IR 550 spectrometer. In situ infrared spectra were acquired using an Applied Systems, Inc. React-IR DiComp Probe. Optical rotations were determined with a Perkin-Elmer 241 polarimeter. NMR data was acquired on Bruker instruments. Coupling constants are given in hertz.

EXAMPLE 1

General Procedure for the Preparation of Bis (iodomethyl)zinc 8

Method A

Diethylzinc (1 equiv.) was added to THF (1.8 mL/mmol diethylzinc) at $T_i$ −60° C. Diiodomethane (2 equiv.) was added to this solution at $T_i$ −60° C. The bath was removed, and the solution was allowed to warm to $T_i$=0° C., whereupon it was immersed in an ice bath. After stirring 60 min at 0° C, the solution was cooled to $T_i$ −70° C. and used as is.

Method B

Diethylzinc (1 equiv.) was added to THF (3.4 mL/mmol diethylzinc) at $T_i$ −60° C. Diiodomethane (2 equiv.) was added to this solution at $T_i$ −60° C. The bath was removed, and the solution was allowed to warm to $T_i$=40° C. After stirring at −40° C. for 70–90 min, the solution was cooled to $T_i$ −70° C. and used as is.

EXAMPLE 2

General Procedure for the Preparation of Solutions of Zinc Homoenolates 13a and 14a, and Conversion to the Corresponding Titanium Homoenolates To a solution of amide 1 (7.50 g, 23.3 mmol) in THF (45 mL) was added 2.5 M nBuLi (9.6 mL, 24 mmol) at $T_i$ −65° C. After 10–30 min, the solution of lithium enolate 7 was gradually cannulated into a solution of bis(iodomethyl)zinc 8 (25 mmol prepared by Method A, or 14 mmol prepared by Method B) in THF (45 mL) at $T_i$ −70° C. (bath T=−80° C.), generating a solution of enolate zincate 11. In another flask, 2.5 M nBuLi was added to a solution of benzyl alcohol (7.2 mL, 69 mmol) and a few crystals of 1,10-phenanthroline in THF (45 mL) at $T_i$ −20° C. until a brown color developed. After cooling the lithium benzyl alkoxide solution to −78° C., it was then cannulated into the solution of enolate zincate 11 such that $T_i$ −75° C. The solution was allowed to warm to −70° C. and stirred overnight.

A 1.0 M solution of $TiCl_4$ (35 mL, 35 mmol) was added to THF (10 mL) at $T_i$ 0° C. (bath T=−45° C.), resulting in the formation of a precipitate. After cooling the mixture to $T_i$=40° C., $T_i(OiPr)_4$ (3.6 mL, 12 mmol) was added such that $T_i$ −25° C. The mixture was removed from the cooling bath and warmed to rt. The precipitate dissipated upon reaching $T_i$=−20° C., generating a yellow-green solution of $Cl_3Ti$ (OiPr).

The heterogeneous mixture of homoenolate 13a was cooled to $T_i$=−80° C., whereupon the solution of $Cl_3Ti(OiPr)$ was added by cannula such that $T_i$ −67° C. The, now homogenous, deep red solution was removed from the bath and allowed to warm to $T_i$=−20° C., where it was then maintained until used further. Samples of the titanium homoenolate solution were analyzed by HPLC to determine molarity and percent conversion (corrected for response factors).

An aliquot of the titanium homoenolate (typically 50.0 mL) was transferred to a flask at $T_i$ −20° C., to which was added the aldehyde. After stirring for the specified time, the mixture was quenched by pouring into ⅓-saturated $Na_2CO_3$ (300 mL). The aqueous was extracted with MTBE (3X). The combined organic extracts were washed with saturated NaHCO$_3$ and brine, then concentrated via rotary evaporation. The crude oil was taken up in 4:1 hexanes/MTBE (100 mL). This solution was washed with 30% MeOH in H$_2$O (5×100 mL) and brine, then dried over MgSO$_4$. The resultant crude was further purified by chromatography.

EXAMPLE 3

[3aS-[3(1R*,2S*,4S*),3aα,8aα]]-N-[2-hydroxy-5-oxo-1,4-di(phenylmethyl)-5-(8,8a-dihydro-2,2-dimethyl-2H-indeno[1,2-d]oxazol-3(3aH)-yl)pentyl]carbamic acid 1,1-dimethylethyl ester (4a).

A solution of N-tert-Boc-L-phenylalanine (435 mg, 1.74 mmol) in CH$_2$Cl$_2$ (3.0+2.0 mL) was added to a 0.071 M (75% conversion) solution of titanium homoenolate (50.0 mL, 3.55 mmol) at −20° C. The solution was stirred at −20° C. for 3 days. After workup, the crude was purified by chromatography on silica gel (3:1 Hex/EtOAc) yielding 4a (604 mg, 80%).: R$_F$ 0.25 (4:1-hexane:ethyl acetate); $^1$H NMR (300 MHz, CDCl$_3$) δ 7.37–7.10 (m, 12H), 6.84–6.79 (m, 1H), 6.10 (d, J=7.2 Hz, 1H), 5.45 (m, 1H), 4.78 (m, 1H), 4.68 (m, 1H), 4.00 (m, 1H), 3.89 (m, 1H), 3.78 (m, 1H), 3.48–3.39 (m, 1H), 3.30–3.21 (m, 1H), 3.025 (m, 2H), 2.81–2.75 (m, 3H), 1.80–1.74 (m, 2H), 1.64 (s, 3H), 1.38 (br s, 9H), 1.31 (s, 3H); $^{13}$C NMR (62.9 MHz, CDCl$_3$) δ 172.50, 156.82, 140.756, 140.33, 140.18, 137.49, 129.67, 129.10, 128.67, 128.53, 128.41, 127.98, 127.03, 126.96, 126.72, 126.62, 125.43, 124.15, 96.45, 80.17, 79.04, 72.13, 65.28, 57.68, 44.71, 37.62, 36.52, 36.17, 28.24, 26.56, 23.84; IR (neat) 3417, 3362, 2980, 2935, 1688, 1623, 1435, 1159 cm$^{-1}$; MS (CI) m/e 585 (9, M++H), 511 (46), 364 (98), 322 (100), 236 (61); [α]$_D^{20}$ +71.2°(c=1.05, CHCl$_3$); Analysis calc'd for C$_{36}$H$_{44}$N$_2$O$_5$: C, 73.94; H, 7.58; N, 4.79; found: C, 73.93; H, 7.67; N, 4.46.

EXAMPLE 4

[3aS-[3(1R*, 2S*, 4S*), 3aα,8aα]]-[2-hydroxy-5-oxo-1-methyl-4-phenylmethyl-5-(8,8a-dihydro-2,2-dimethyl-2H-indenol[1,2-d]oxazol-3(3aH)-yl)pentyl]carbamic acid 1,1-dimethylethyl ester (4b).

A solution of N-tert-Boc-L-alaninal (295 mg, 1.62 mmol) in CH$_2$Cl$_2$ (3.0+2.0 mL) was added to a 0.077 M (81% conversion) solution of titanium homoenolate (50.0 mL, 3.85 mmol) at −20° C. The solution was stirred at −20° C. for 3 days. After workup, the crude was purified by chromatography on silica gel (6:1→1:1 Hex/EtOAc) yielding 4b (437 mg, 53%).: R$_F$ 0.21 (2:1-hexane:ethyl acetate); $^1$H NMR (300 MHz, CDCl$_3$) δ 7.37–7.13 (m, 7H), 6.85–6.79 (m, 1H), 6.10 (d, J=7.6 Hz, 1H), 5.46 (d, J=4.0 Hz, 1H), 4.79 (t, J=3.0 Hz, 1H), 4.62 (d, J=6.9 Hz, 1H), 3.82–3.68 (m, 2H), 3.62-3.51 (m, 1H), 3.47–3.38 (m, 1H), 3.34–3.21 (m, 1H), 3.14–2.96 (m, 2H), 2.78 (dd, J=12.8, 4.3 Hz, 1H), 1.69–1.65 (m, 2H), 1.64 (s, 3H), 1.44 (s, 9H), 1.31 (s, 3H), 1.08 (d, J=6.9 Hz, 3H); $^{13}$C NMR (62.9 MHz, CDCl$_3$) δ 172.34, 156.57, 140.75, 140.34, 140.16, 129.64, 128.62, 127.96, 127.01, 126.58, 125.40, 124.16, 96.44, 79.92, 79.04, 73.06, 65.30, 51.76, 44.63, 37.72, 36.84, 36.15, 28.34, 26.55, 23.88; IR (neat) 3352, 2976, 2929, 1689, 1624, 1498, 1426, 1365, 1204; MS (CI) m/e 509 (7, M++H), 435 (46), 364 (100); 220 (43).

EXAMPLE 5

[3aS-[3(2S* ,4S*),3aα,8aα]]-3,3a,8,8a-tetrahydro-3-[4-hydroxy-1-oxo-4-phenyl-2-(phenylmethyl)butyl]-2,2-dimethyl-2H-indeno[1,2-d]oxazole (4c)

To a 0.064 M (67% conversion) solution of titanium homoenolate (60.0 mL, 3.84 mmol) at −40° C. was added benzaldehyde (1.9 mL, 18.7 mmol). The solution was stirred at −40° C. for 2 days. After workup, the crude was purified by chromatography on silica gel (5:1→2:1 Hex/EtOAc) yielding fractions containing a single epimer of 4c (703 mg), and fractions containing a mixture of major/minor epimers (400 mg). The combined yield=50% (76% based on 13a).: R$_F$ 0.31 (2:1-hexane:ethyl acetate); $^1$H NMR (250 MHz, CDCl$_3$) δ 7.41–7.12 (m, 12H), 6.88–6.81 (m, 1H), 6.12 (d, J=7.8 Hz, 1H), 5.33 (d, J=4.3 Hz, 1H), 4.85–4.76 (m, 2H), 3.47 (dd, J=12.1, 9.2 Hz, 1H), 3.43–3.33 (m, 1H), 3.03–3.01 (m, 2H), 2.98 (dd, J=12.1, 3.6 Hz, 1H), 2.34 (d, 3.4H, 1 (OH)), 2.04–1.98 (m, 2H), 1.61 (s, 3H), 1.30 (s, 3H); $^{13}$C NMR (62.9 MHz, CDCl$_3$) δ 172.2, 144.8, 140.8, 140.5, 140.4, 129.7, 128.7, 128.6, 128.0, 127.7, 127.1, 126.6, 125.7, 125.5, 124.2, 96.5, 79.1, 71.8, 65.2, 45.1, 43.2, 37.3, 36.1, 26.6, 23.9; IR (neat) 3408, 3075, 3025, 1626, 1055 cm$^{-1}$; MS (CI) MS (CI) m/e 442 (100, M++H), 440 (56, M+−H), 424 (64), 322 (100); [α]$_D^{20}$ 143° (c=1.31, CHCl$_3$); Analysis calc'd for C$_{29}$H$_{33}$NO$_3$: C, 78.88; H, 7.08; N, 3.17; found: C, 78.68; H, 7.19; N, 3.20.

EXAMPLE 6

[3aS-[3(2S*, 4S*), 3aα,8aα]]-3,3a,8,8a-tetrahydro-3-[4-hydroxy-5-methyl-1-oxo-2-(phenytmethyl)-5-hexenyl]-2,2-dimethyl]-2H-indeno[1,2-d]oxazole (4d)

To a 0.071 M (74% conversion) solution of titanium homoenolate (50.0 mL, 3.55 mmol) at −40° C. was added methacrolein (1.5 mL, 18.1 mmol). The solution was stirred at −40° C. for 4 days. After workup, the crude was purified by chromatography on silica gel (5:1 Hex/EtOAc), yielding fractions containing 9 (300 mg, 0.89 mmol), and fractions containing 4d as an 88:12 mixture of epimers (860 mg, 2.12 mmol). The combined yield =45% overall (55% based on recovered 9).: R$_F$ 0.40 (2:1-hexane:ethyl acetate); $^1$H NMR (300 MHz, CDCl$_3$) δ 7.39–7.11 (m, 7H), 6.86–6.80 (m, 1H), 6.13 (d, J=7.6 Hz, 1H), 5.46 (d, J=4.4 Hz, 1H), 4.99 (m, 1H), 4.86-4.80 (m, 2H), 4.15 (d, 9.3H), 3.48–3.37 (m, 1H), 3.33–3.22 (m, 1H), 3.18-2.99 (m, 2H), 2.83 (dd, J=12.9, 4.2 Hz, 1H), 1.98–1.69 (m, 3H), 1.73 (s, 3H), 1.64 (s, 3H), 1.31 (s, 3H); $^{13}$C NMR (62.9 MHz, CDCl$_3$) δ 172.08, 147.93, 140.84, 140.40, 140.35, 129.64, 128.62, 127.99, 127.04, 126.56, 125.45, 124.18, 110.57, 96.45, 79.01, 73.36, 65.25, 44.85, 39.59, 37.41, 36.18, 26.55, 23.92, 18.25; IR (neat) 3416, 2983, 2938, 1626, 1431, 1243, 1224, 1206, 1051 cm$^{-1}$; MS (CI) m/e 406 (97 M++H), 404 (100, M+−H)), 388 (41); [α]$_D^{20}$ +123.1° (c=1.03, CHCl$_3$); Analysis calc'd for C$_{26}$H$_{31}$NO$_3$: C, 77.01; H, 7.70; N, 3.45; found: C, 76.86; H, 7.77; N, 3.19.

EXAMPLE 7

[3aS-[3(2S*, 4S*), 3aα,8aα]]-3-[4-cyclohexyl-4-hydroxy-1-oxo-2-(phenyltnethyl)butyl]-3,3a,8,8a-tetrahydro-2,2-dimethyl]-2H-indeno[1,2-d]oxazole (4e)

To a 0.071 M (74% conversion) solution of titanium homoenolate (50.0 mL, 3.55 mmol) at −40° C. was added cyclohexanecarboxaldehyde (1.5 mL, 18.1 mmol). The solution was stirred at −40° C. for 4 days. After workup, the crude was purified by chromatography on silica gel (6:1 Hex/EtOAc), yielding fractions containing 9 (220 mg, 0.65 mmol), and fractions containing 4e as a single isomer (1.16 g, 55% overall, 73% based upon 13a).: R$_F$ 0.52 (2:1-hexane:ethyl acetate); $^1$H NMR (300 MHz, CDCl$_3$) δ 7.37–7.09 (m, 7H), 6.82–6.75 (m, 1H), 6.02 (d, J=7.7 Hz, 1H), 5.44 (d, J=4.3 Hz, 1H), 4.83–4.79 (m, 1H), 3.52–2.95 (m, 5H), 2.75 (dd, J=12.8, 3.6 Hz, 1H), 1.88–1.54 (m, 8H), 1.64 (s, 3H), 1.41–0.92 (m, 6H), 1.30 (s, 3H); $^{13}$C NMR (62.9 MHz, CDCl$_3$) δ 172.42, 140.85, 140.65, 140.34, 129.66, 128.58, 127.90, 126.99, 126.48, 125.36, 124.20, 96.33, 79.02, 74.12, 65.09, 45.23, 44.59, 38.49, 37.18, 36.15, 29.11, 28.38, 26.55, 26.46, 26.10, 23.90; IR (neat) 3429, 2924, 2852, 1625, 1427, 1206, 1148, 1051 cm$^{-1}$; MS (CI) m/e 448 (87, M++H), 446 (49, M+−H), 322 (100), 276 (75), 259 (84); [α]$_D^{20}$ +105.6° (c=1.02, CHCl$_3$); Analysis calc'd for C$_{29}$H$_{37}$NO$_3$: C, 77.82; H, 8.33; N, 3.13; found: C, 77.80; H, 8.16; N, 3.03.

EXAMPLE 8

[3aS-[3(2S* ,4S*),3aα,8aα]]-3,3a,8,8a-tetrahydro-3-[4-hydroxy-5-methyl-1-oxo-2-(phenylmethyl)hexyl]-2,2-dimethyl-2H-indeno[1,2-d]oxazole (4f)

To a 0.075 M (72% conversion) solution of titanium homoenolate (50.0 mL, 3.74 mmol) at −50° C. was added isobutyraldehyde (3.4 mL, 37.4 mmol). The solution was stirred at −50° C. for 3.6 days. After workup, the crude was purified by chromatography on silica gel (4:1→2:1 Hex/EtOAc), yielding fractions containing a single epimer of 4f (580 mg), and fractions containing a mixture of major/minor epimers (541 mg). The combined yield=53% (74% based on 13a).: R$_F$ 0.31 (2:1-hexane:ethyl acetate); $^1$H NMR (250 MHz, CDCl$_3$) δ 7.41–7.06 (m, 7H), 6.84–6.76 (m, 1H), 6.04 (d, J=7.6 Hz, 1H), 5.45 (d, J=4.4 Hz, 1H), 4.83–4.81 (m, 1H), 3.52–3.42 (m, 1H), 3.42 (dd, J=13.0, 9.7 Hz, 1H), 3.30–3.20 (m, 1H), 3.05–3.04 (m, 2H), 2.76 (dd, J=13.0, 3.8 Hz, 1H), 1.86–1.76 (m, 1H), 1.71–1.56 (m, 2H), 1.65 (s, 3H), 1.31 (s, 3H), 0.93 (d, J=6.7 Hz, 3H), 0.92 (d, J=6.8 Hz, 3H); $^{13}$C NMR (62.9 MHz, CDCl$_3$) δ 172.5, 140.78, 140.64, 140.32, 129.7, 128.6, 127.9, 127.0, 126.5, 125.4, 124.2, 96.3, 79.0, 74.6, 65.1, 45.3, 38.4, 37.1, 36.1, 34.7, 26.6, 23.9, 18.7, 17.9; IR (neat) 3429, 3075, 3025, 1625, 1051 cm$^{-1}$; MS (CI) m/e 408 (100, M++H), 236 (17); [α]$_D^{20}$ 110° (c=1.21, CHCl$_3$); Analysis calc'd for C$_{26}$H$_{33}$NO$_3$: C, 76.62; H, 8.16; found: C, 76.27; H, 7.97; N, 3.41.

EXAMPLE 9

[3aS-[3(2S*,4R*),3aα,8aα]]-3,3a,8,8a-tetrahydro-3-[4-hydroxy-1-oxo-2-(phenylmethyl)octyl]-2,2-dimethyl-2H-indeno[1,2-d]oxazole (4g)

To a 0.094 M (77% conversion) solution of titanium homoenolate (50.0 mL, 4.7 mmol) at −20° C. was added n-pentanal (0.62 mL, 5.64 mmol). The solution was stirred at −20° C. for 2.4 days. After workup, the crude was purified by chromatography on silica gel (7:2→3:1 Hex/EtOAc) yielding 4g as a mixture of epimers (1.35 g, 53% overall yield, 68% based on 13a).: R$_F$ 0.35 (2:0-hexane:ethyl acetate); $^1$H NMR (250 MHz, CDCl$_3$) δ 7.39–7.08 (m, 7H), 6.82–6.74 (m, 1H), 6.01 (d, J=7.6 Hz, 1H), 5.47 (d, J=4.4 Hz, 1H), 4.80–4.76 (m, 1H), 3.80–3.68 (m, 1H), 3.38 (dd, J=12.1, 9.7 Hz, 1H), 3.37-3.25 (m, 1H), 3.00–2.97 (m, 2H), 2.77 (dd, J=12.1, 2.9 Hz, 1H), 2.56 (d, 5.0 H, 1 (OH)), 1.85–1.27 (m, 8H), 1.62 (s, 3H), 1.29 (s, 3H), 0.93 (t, J=6.6 Hz, 3H); $^{13}$C NMR (62.9 MHz, CDCl$_3$) δ 172.5, 140.76, 140.61, 140.29, 129.65, 128.60, 127.91, 127.02, 126.36, 125.34, 124.18, 96.3, 79.0, 69.5, 65.1, 45.1, 41.6, 38.5, 37.1, 36.1, 28.2, 26.6, 24.1, 22.8, 14.2; IR (neat) 3415, 3074, 3032, 1624, 1142, 1050 cm$^{-1}$; MS (CI) m/e 422 (100, M++H), 250 (25), 232 (20); [α]$_D^{20}$ 104° (c=1.21, CHCl$_3$); Analysis calc'd for C$_{27}$H$_{35}$NO$_3$: C, 76.92; H, 8.37; N, 3.32; found: C, 77.03; H, 8.39; N, 3.34. [3aS-[3(2S *,4S*),3aα,8aα]]-3,3a,8,8a-tetrahydro-3-[4-hydroxy-1-oxo-2-(phenylmethyl)octyl]-2,2-dimethyl-2H-indeno[1,2-d]oxazole (minor epimer). $^1$H NMR (250 MHz, CDCl$_3$) δ 6.97–6.88 (m, 1H), 6.28 (d, J=7.6 Hz, 1H), 5.80 (d, J=4.3 Hz, 1H), 4.85–4.80 (m, 1H), 3.06–3.01 (m, 2H), 2.32 (d, 5.8H, 1 (OH)); $^{13}$C NMR (62.9 MHz, CDCl$_3$) δ 172.8, 140.90, 139.92, 129.54, 128.66, 96.7, 79.13, 69.265.7, 38.34, 27.9, 24.1, 22.6.

EXAMPLE 10

[3aS-[3(1R*,2S* ,4S*),3aα,8aα-N-[2-hydroxy-5-oxo-4-methyl-1-(phenylmethyl)-5-(8,8a-dihydro-2,2-dimethyl-2H-indeno[1,2-d]oxazol-3(3aH)-yl)pentyl]carbamic acid 1,1-dimethylethyl ester (5a).

A solution of N-tert-BOC-L-phenylalaninal (393 mg, 1.58 mmol) in CH$_2$Cl$_2$ (2.0+1.0 mL) was added to a 0.070 M (73% conversion) solution of titanium homoenolate 14a (545.0 mL, 3.15 mmol) at −20° C. The solution was stirred at −20° C. for 3.5 days. After workup, the crude was purified by chromatography on silica gel (3:1→1:1 Hex/EtOAc) yielding 5a (464 mg, 58%).: R$_F$ 0.13 (3:1 Hex/EtOAc); $^1$H NMR (300 MHz, CDCl$_3$) δ 7.34–7.09 (m, 9H), 5.52–5.42 (m, 1H), 4.89–4.76 (m, 1H), 4.70–4.61 (m 1H), 3.96–3.68 (m, 2H), 3.27–3.13 (m, 1H), 3.11–3.03 (m, 2H), 2.90–2.63 (m, 2H), 2.04–1.51 (m, 6H), 1.41–1.13 (m, 15H); $^{13}$C NMR (62.9 MHz, CDCl$_3$) δ 174.17, 157.24, 141.16, 140.76, 137.65, 129.12, 128.62, 128.44, 127.22, 126.64, 125.87, 124.06, 96.31, 80.03, 78.77, 76.55, 71.91, 65.54, 57.57, 38.14, 36.35, 35.97, 28.22, 27.17, 26.64, 23.77, 17.10; IR (neat) 3386, 2987, 2940, 16971635, 1436, 1360, 1214; MS (CI) m/e 508 (20, M++H), 435 (38), 288 (70), 220 (100), 190 (65); [α]$_D^{20}$ +55.5° (c=1.20, CHCl$_3$); Analysis calc'd for: C, 70.84; H, 7.93; N, 5.51; found: C, 70.89; H, 7.95; N, 5.42.

EXAMPLE 11

[3aS-[3(2S* ,4S*),3aα,8aα]]-3,3a,8,8a-tetrahydro-3-[4-hydroxy-1-oxo-4-phenyl-2-methylbutyl]1-2,2-dimethyl-2H-indeno[1,2-d]oxazole (5c).

Benzaldehyde (1.60 mL, 15.7 mmol) was added to a 0.070 M (73% conversion) solution of titanium homoenolate 14a (45.0 mL, 3.15 mmol) at −40° C. The solution was stirred at −40° C. for 3.5 days. After workup, the crude was purified by chromatography on silica gel (4:1→1:1 Hex/EtOAc) yielding 5c (691 mg, 44% overall, 60% based on 14a).: R$_F$ 0.27 (2:1 Hex/EtOAc); $^1$H NMR (300 MHz, CDCl$_3$) δ 7.34–7.2 (m, 9H), 5.34 (d, J=4.5 Hz, 1H), 4.81–4.74 (m, 2H), 3.33–3.25 (m, 1H), 3.09–3.07 (m, 2H), 2.74–2.73 (m, 1H), 2.13–1.99 (m, 1H), 1.88–1.76 (m, 1H), 1.55 (s, 3H), 1.41, (d, J=6.5 Hz, 3H), 1.33 (s, 3H); $^{13}$C NMR (62.9 MHz, CDCl$_3$) δ 173.78, 144.56, 141.22, 140.77, 128.58, 128.44, 127.67, 127.22, 125.89, 125.62, 124.05, 96.34, 78.75, 71.94, 65.49, 44.18, 36.34, 26.62, 17.09, 14.19; IR (neat) 3394, 2987, 2933, 1628, 1421, 1206, 1152, 1052; MS (CI) m/e 365 (100, M++H), 348 (50), 190 (9), 174 (20); [α]$_D^{20}$ +147.4° (c=1.16, CHCl$_3$); Analysis calc'd for: C, 75.59; H, 7.45; N, 3.83; found: C, 75.72; H, 7.40; N, 3.80.

EXAMPLE 12

C[3aS-[3(2S*,4S*), 3aα,8aα]]-3-[4-cyclohexyl-4-hydroxy-1-oxo-2-methylbutyl]-3,3a,8,8a-tetrahydro-2,2-dimethyl]-2H-indeno[1,2-d]oxazole (5e)

Cyclohexanecarboxaldehyde (1.9 mL, 15.4 mmol) was added to a 0.070 M (73% conversion) solution of titanium homoenolate 14a (45.0 mL, 3.15 mmol) at −40° C. The solution was stirred at −40° C. for 3.5 days, then warmed to −30° C. and stirred an additional 24 h. After workup, the crude was purified by chromatography on silica gel (3:1→1:1 Hex/EtOAc) yielding 5e (660 mg, 41%, 56% based upon 14a).: R$_F$ 0.24 (4:1 Hex/EtOAc); $^1$H NMR (300 MHz, CDCl$_3$) δ 7.33–7.18 (m, 4H), 5.48 (d, J=4.8 Hz, 1H), 4.89–4.82 (m, 1H), 3.48–3.38 (m, 1H), 3.27–3.16 (m, 1H), 3.1 (m, 2H), 1.85–1.49 (m, 9H), 1.63 (s, 3H), 1.38 (s, 3H), 1.36 (d, J=6.4 Hz, 3H), (1.36–1.11 (m, 3H), 1.10–0.88 (m, 2H); $^{13}$C NMR (62.9 MHz, CDCl$_3$) δ 174.42, 141.33, 140.81, 128.40, 127.20, 125.88, 124.06, 96.26, 78.75, 74.34, 65.47, 44.52, 39.50, 36.36, 29.04, 28.28, 26.64, 26.42, 26.14, 26.06, 23.75, 16.95; IR (neat) 3409, 2925, 2856, 1636, 1426, 1214, 1145, 1045; MS (CI) m/e 371 (100, M++H), 354 (18), 200 (30), 174 (20); $[\alpha]_D^{20}$ +108.8° (c=1.21, CHCl$_3$); Analysis calc'd for: C, 74.36; H, 8.95; N, 3.77; found: C, 74.61; H, 8.78; N, 3.72.

EXAMPLE 13

[3aS-[3(R*),3aα,8aα]]-3,3a,8,8a-tetrahydro-2,2-dimethyl-3-[1-oxo-2-(phenylmethvl)propyl]-2H-indeno[1,2-d]oxazole (9)

To a solution of amide 1 (400 mg, 1.24 mmol) in THF (5 mL) at T$_i$ -70° C. was added 1.5 M nBuLi (0.87 mL, 1.3 mmol). The deep yellow solution containing 7 was stirred 40 min at -78° C., then cooled to -90° C. In a separate flask, a solution of 1.5 M nBuLi (6.8 mL, 10 mmol) was added to benzyl alcohol (1.0 mL, 9.7 mmol) in THF (12 mL) at T$_i$ -20° C. Of this 0.5 M solution of lithium benzyl alkoxide, an aliquot (7.8 mL, 3.9 mmol) was added to the solution of lithium enolate 7. A preformed 1.0 M solution of bis (iodomethyl)zinc 8 (Method A) in THF (1.3 mL) was then added such that T$_i$ -80° C. The solution was warmed to -78° C., and stirred for 3.5 h. The reaction was quenched by the addition of MeOH (1 mL), followed by saturated NaHCO$_3$, at -78° C. After warming to rt, the aqueous was extracted with MTBE (2X). The combined organic extracts were washed with saturated NaHCO$_3$ and brine, then dried over MgSO$_4$. The resultant crude oil (900 mg) was chromatographed on silica gel (4:1 Hex/EtOAc), yielding 9 (325 mg, 78%).: R$_F$ 0.26 (3:1-hexane:ethyl acetate); $^1$H NMR (250 MHz, CDCl$_3$) δ 7.38–7.16 (m, 7H), 6.97–6.88 (m, 1H), 6.33 (d, J=7.8 Hz, 1H), 5.18 (d, J=4.4 Hz, 1H), 4.87–4.82 (m, 1H), 3.42 (dd, J=13.1, 8.3 Hz, 1H), 3.11–3.04 (m, 2H), 2.74–2.65 (dd, J=13.1, 5.5 Hz, 1H), 1.63 (s, 3H), 1.34 (s, 3H), 1.28 (d, J=6.9 Hz, 3H); $^{13}$C NMR (62.9 MHz, CDCl$_3$) δ 172.3, 140.41, 140.36, 129.4, 128.4, 127.1126.4, 125.5, 124.0, 96.4, 78.8, 65.3, 42.4, 39.2, 36.2, 26.5, 23.9, 18.6; IR (neat) 3067, 3018, 1649, 1151, 1053 cm$^{-1}$; MS (CI) m/e 336 (100, M++H); $[\alpha]_D^{20}$ +199° (c=1.20, CHCl$_3$); Analysis calc'd for C$_{22}$H$_{26}$NO$_2$: C, 78.54; H, 7.79; N, 4.16; found: C, 78.59; H, 7.57; N, 4.20.

EXAMPLE 14

[3aS-[3(R*),3aα,8aα]]-3,3a,8,8a-tetrahydro-2,2-dimethyl-3-[1-oxo-2-(phenylmethyl)butyl]-2H-indeno[1,2-d]oxazole (10)

To a solution of amide 1 (400 mg, 1.24 mmol) in THF (4 mL) was added 1.5 M nBuLi (0.87 mL, 1.3 mmol) at T$_i$ -65° C. The solution was stirred >60 min at -78° C., whereupon ethyl iodide (0.50 mL, 6.2 mmol) was added. After stirring at -78° C. for 50 min, the reaction was quenched with MeOH (1 mL), followed by brine. After warming to rt, the aqueous was extracted with MTBE (2X). The combined organic extracts were washed with saturated NaHCO$_3$ and brine, then dried over MgSO$_4$. A portion of the crude material (244 rmg) was purified by chromatography on silica gel (4:1 hexanes/EtOAc), yielding 10 (209 mg).: R$_F$ 0.33 (3:1-hexane:ethyl acetate); $^1$H NMR (250 MHz, CDCl$_3$) δ 7.38–7.13 (m, 7H), 6.90–6.82 (m, 1H), 6.13 (d, J=7.7 Hz, 1H), 5.27 (d, J=4.4 Hz, 1H), 4.84–4.80 (m, 1H), 3.39 (dd, J=13.1, 8.8 Hz, 1H), 3.12–2.93 (m, 3H), 2.76 (dd, J=13.1, 4.8 Hz, 1H), 1.80–1.69 (m, 2H), 1.67 (s, 3H), 1.33 (s, 3H), 1.07 (t, 7.4. 3H); $^{13}$C NMR (62.9 MHz, acetone-d$_6$) δ 171.9142.0, 141.8, 141.6, 130.4, 129.2, 128.5, 127.5, 127.1, 126.0, 124.9, 96.7, 79.7, 66.1, 49.5, 38.0, 36.5, 27.7, 27.0, 24.2, 11.5; IR (neat) 3067, 3025, 1640, 1144, 1060 cm$^{-1}$; MS (CI) m/e 350 (100, M++H); $[\alpha]_D^{20}$ 138° (c=1.03, CHCl$_3$); Analysis calc'd for C$_{23}$H$_{28}$NO$_2$: C, 78.82; H, 8.05; N, 4.00; found: C, 79.00; H, 7.90; N, 3.91.

EXAMPLE 15

[2R-[2a(S*),4a]]-[2-phenyl-1-(tetrahydro-5-oxo-4-(phenylmethyl-2-furanylethyl]carbamic acid 1,1-dimethylethyl ester (15a)

To a solution of 4a (106 mg, 0.181 mmuol) in a toluene/CH$_2$Cl$_2$ solution (5.3 mL/0.9 mL) was added p-toluenesulfonic acid monohydrate (34 mg, 0.18 mmol). The solution was stirred overnight at rt. Toluene was added to the slurry, and the mixture was filtered, washing with toluene (2×5 mL). Drying the solid yielded 13 (51 mg, 87%) The combined organic filtrates were washed with H$_2$O (2×), saturated NaHCO$_3$, and brine, then dried over Na$_2$SO$_4$. The resultant crude was chromatographed on silica gel (6:1 Hex/EtOAc), yielding 15a (56 mg, 82%).: R$_F$ 0.30 (4:1-hexane:ethyl acetate); $^1$H NMR (300 MHz, CDCl$_3$) δ 7.33–7.15 (m, 10H), 4.37 (m, 1H), 4.26 (m, 1H), 3.90 (m, 1H), 3.28 (dd, J=13.7, 3.9 Hz, 1H), 295–2.67 (m, 4H), 2.28–2.17 (m, 1H), 1.78 (dd, J=23.3, 11.6 Hz, 1H), 1.35 (b s, 9H); $^{13}$C NMR (62.9 MHz, CDCl$_3$) δ 177.58, 155.19, 138.39, 136.65, 129.49, 128.83, 128.68, 128.59, 126.72, 79.91, 78.95, 54.38, 42.49, 36.12, 31.36, 28.20; IR (neat) 3355, 2982, 2929, 1773, 1707, 1498, 1366, 1168 cm$^{-1}$; $[\alpha]_D^{20}$ -81.3° (c=1.04, CHCl$_3$); Analysis calc'd for C$_{15}$H$_{19}$NO$_2$: C, 73.44; H, 7.81; N, 5.71; found: C, 73.47; H, 7.76; N, 5.66.

EXAMPLE 16

(3R-cis)-dihydro-5-phenyl-3-(phenylmethyl)-2(3H)-furanone (15e).

To a solution of 4e (100 mg, 0.228 mmol) in toluene (5 mL) was added p-toluenesulfonic acid monohydrate (43 mg, 0.23 mmol). The solution was stirred overnight at rt. The mixture was filtered, washing with toluene (2×2 mL). Drying the solid yielded 16 (66 mg, 90%). The combined organic filtrates were concentrated, and the resultant crude was chromatographed on silica gel (11:1 Hex/EtOAc), yielding 15e (46 mg, 80%).: R$_F$ 0.41 (6:1-hexane:ethyl acetate); $^1$H NMR (300 MHz, CDCl$_3$) δ 7.18–7.38 (m, 10H), 5.32 (dd, J=10.6, 5.8 Hz, 1H), 3.35 (dd, J=13.8, 4.1 Hz, 1H), 3.0–3.13 (m, 1H), 2.77 (dd, J=13.8, 9.7 Hz, 1H), 2.55–2.66 (m, 1H), 1.92 (dd, J=12.5, 10.6 Hz, 1H); $^{13}$C NMR (62.9 MHz, CDCl$_3$) δ 177.68, 139.02,138.47, 128.84, 128.71, 128.49, 126.73, 125.43, 124.36, 79.48, 43.35, 37.53, 32.12; IR (neat) 3030, 2921, 2858, 1761, 1497, 1455, 1166 cm$^{-1}$; MS (CI) m/e 270 (100, M++NH$_4$), 253 (10, M++H), 235 (17); $[\alpha]_D^{20}$ -117.3° (c=1, CHCl$_3$); Analysis calc'd for C$_{17}$H$_{16}$O$_2$: C, 80.93; H, 6.39; found: C, 80.69; H, 6.49.

EXAMPLE 17

(3R-cis)-dihydro-5-(1-methylethyl)-2-(phenylmethyl)-2(3H)-furanone (15h)

To a solution of 4h (108 mg, 0.266 mmol) in toluene (5.5 mL) was added p-toluenesulfonic acid monohydrate (51 mg, 0.27 mmol). The solution was stirred overnight at rt. The mixture was filtered, washing with toluene (2×5 mL). Drying the solid yielded 16 (77 mg, 90%) The combined organic filtrates were washed with H$_2$O (2×), saturated NaHCO$_3$, and brine, then dried over Na$_2$SO$_4$. The resultant crude was chromatographed on silica gel (11:1 Hex/EtOAc), yielding 15h (48 mg, 85%).: R$_F$ 0.32 (10:1 Hex/EtOAc); $^1$H NMR (300 MHz, CDCl$_3$) δ 7.34–7.18 (m, 5H), 4.05–3.95 (m, 1H), 3.29 (dd, J=13.8, 4.0 Hz, 1H), 2.98–2.84 (m, 1H), 2.69 (dd, J=13.8, 9.7 Hz, 1H), 2.26–2.16 (m, 1H), 1.82–1.1.68 (m, 1H), 1.64–1.25 (m, 1H), 0.98 (d, J=6.7 Hz, 3H), 0.85 (d, J=6.7 Hz, 3H); $^{13}$C NMR (62.9 MHz, CDCl$_3$) δ 178.12, 138.71, 128.79, 128.65, 126.62, 83.80, 42.98, 36.15, 32.88, 32.36, 18.60, 17.18; IR (neat) 2964, 2929, 2877, 1768, 1454, 1176, 1016, 965 cm$^{-1}$; MS (CI) m/e 236 (100, M++NH$_4$), 219 (92, M++H); $[\alpha]_D^{20}$ –104.3° (c=1.05, CHCl$_3$); Analysis calc'd for C$_{14}$H$_{18}$O$_2$: C, 77.03; H, 8.31; found: C, 77.15; H, 8.39.

EXAMPLE 18

[3aS-[3(1R*,2*,4S*),3aα,8aα]]-N-[2-hydroxy-5-oxo-4-methyl-1-(phenylmethyl)-5-(8,8a-dihydro-2,2-dimethyl-2H-indeno[1,2-d]oxazol-3(3aH)-yl)pentyl]carbamic acid 1,1-dimethylethyl ester (5a)

A solution of N-tert-Boc-L-phenylalaninal (393 mg, 1.58 mmol) in CH$_2$Cl$_2$ (2.0+1.0 mL) was added to a 0.070 M (73% conversion) solution of titanium homoenolate 14a (545.0 mL, 3.15 mmol) at –20° C. The solution was stirred at –20° C. for 3.5 days. After workup, the crude was purified by chromatography on silica gel (3:1→1:1 Hex/EtOAc) yielding 5a (464 mg, 58%).: R$_F$ 0.13 (3:1 Hex/EtOAc); $^1$H NMR (300 MHz, CDCl$_3$) δ 7.34–7.09 (m, 9H), 5.52– 5.42 (m, 1H), 4.89–4.76 (m, 1H), 4.70–4.61 (m 1H), 3.96–3.68 (m, 2H), 3.27–3.13 (m, 1H), 3.11–3.03 (m, 2H), 2.90–2.63 (m, 2H), 2.04–1.51 (m, 7H), 1.41–1.13 (m, 15H); $^{13}$C NMR (62.9 MHz, CDCl$_3$) a 174.17, 157.24, 141.16, 140.76, 137.65, 129.12, 128.62, 128.44, 127.22, 126.64, 125.87, 124.06, 96.31, 80.03, 78.77, 76.55, 71.91, 65.54, 57.57, 38.14, 36.35, 35.97, 28.22, 27.17, 26.64, 23.77, 17.10; IR (neat) 3386, 2987, 2940, 16971635, 1436, 1360, 1214; MS (CI) m/e 508 (20, M++H), 435 (38), 288 (70), 220 (100), 190 (65); $[\alpha]_D^{20}$ +55.5°; (c=1.20, CHCl$_3$); Analysis calc'd for: C, 70.84; H, 7.93; N, 5.51; found: C, 70.89; H, 7.95; N, 5.42.

EXAMPLE 19

[3aS-[3(2S*,4S*),3aα,8aα]]-3,3a,8,8a-tetrahydro-3-[4-hydroxy-1-oxo-4-phenyl-2-methylbutyl]-2,2-dimethyl-2H-indeno[1,2-d]oxazole (5c).

Benzaldehyde (1.60 mL, 15.7 mmol) was added to a 0.070 M (73% conversion) solution of titanium homoenolate 14a (45.0 mL, 3.15 mmol) at –40° C. The solution was stirred at –40° C. for 3.5 days. After workup, the crude was purified by chromatography on silica gel (4:1→1:1 Hex/EtOAc) yielding 5c (691 mg, 44% overall, 60% based on 14a).: R$_F$ 0.27 (2:1 Hex/EtOAc); $^1$H NMR (300 MHz, CDCl$_3$) δ 7.34–7.2 (m, 9H), 5.34 (d, J=4.5 Hz, 1H), 4.81–4.74 (m, 2H), 3.33–3.25 (m, 1H), 3.09–3.07 (m, 2H), 2.74–2.73 (m, 2H), 2.13–1.99 (m, 1H), 1.88–1.76 (m, 1H), 1.55 (s, 3H), 1.41, (d, J=6.5 Hz, 3H), 1.33 (s, 3H); $^{13}$C NMR (62.9 MHz, CDCl$_3$) δ 173.78, 144.56, 141.22, 140.77, 128.58, 128.44, 127.67, 127.22, 125.89, 125.62, 124.05, 96.34, 78.75, 71.94, 65.49, 44.18, 36.34, 26.62, 17.09, 14.19; IR (neat) 3394, 2987, 2933, 1628, 1421, 1206, 1152, 1052; MS (CI) m/e 365 (100, M++H), 348 (50), 190 (9), 174 (20); $[\alpha]_D^{20}$+147.4° (c=1.16, CHCl$_3$); Analysis calc'd for : C, 75.59; H, 7.45; N, 3.83; found: C, 75.72; H, 7.40; N, 3.80.

EXAMPLE 20

C[3aS-[3(2S*, 4S*), 3aα,8aα]]-3-[4-cyclohexyl-4-hydroxy-1-oxo-2-methylbutyl]-3,3a,8,8a-tetrahydro-2,2-dimethyl]-2H-indeno[1,2-d]oxazole (5e)

Cyclohexanecarboxaldehyde (1.9 mL, 15.4 mmol) was added to a 0.070 M (73% conversion) solution of titanium homoenolate 14a (45.0 mL, 3.15 mmol) at –40° C. The solution was stirred at –40° C. for 3.5 days, then warmed to –30° C. and stirred an additional 24 h. After workup, the crude was purified by chromatography on silica gel (3:1→1:1 Hex/EtOAc) yielding 5e (660 mg, 41%, 56% based upon 14a).: R$_F$ 0.24 (4:1 Hex/EtOAc); $^1$H NMR (300 MHz, CDCl$_3$) δ 7.33–7.18 (m, 4H), 5.48 (d, J=4.8 Hz, 1H), 4.89–4.82 (m, 1H), 3.48–3.38 (m, 1H), 3.27–3.16 (m, 1H), 3.1 (m, 2H), 1.85–1.49 (m, 9H), 1.63 (s, 3H), 1.38 (s, 3H), 1.36 (d, J=6.4 Hz, 3H), (1.36–1.11 (m, 3H), 1.10–0.88 (m, 2H); $^{13}$C NMR (62.9 MHz, CDCl$_3$) δ 174.42, 141.33, 140.81, 128.51, 128.40, 127.56, 127.20, 125.88, 124.06, 96.26, 78.75, 74.34, 65.47, 65.25, 44.52, 39.50, 36.36, 29.04, 28.28, 26.64, 26.42, 26.14, 26.06, 23.75, 16.95; IR (neat) 3409, 2925, 2856, 1636, 1426, 1214, 1145, 1045; MS (CI) m/e 371 (100, M++H), 354 (18), 200 (30), 174 (20); $[\alpha]_D^{20}$+108.8° (c=1.21, CHCl$_3$); Analysis calc'd for: C, 74.36; H, 8.95; N, 3.77; found: C, 74.61; H, 8.78; N, 3.72.

EXAMPLE 21

Example of Copper(I) Coupling of Homoenolate with Alkyl Halide:

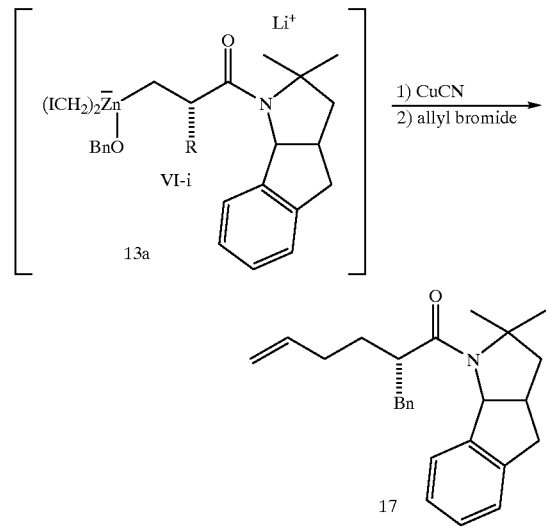

A 0.090 M solution of zinc homoenolate 13a (12 mL, 1.06 mmol) was added to CuCN (130 mg, 1.44 mmol) in THF (10 mL) at –65° C. The mixture was allowed to warm to 0° C. and stirred 5 min. The, now nearly homogenous, solution was cooled to –60° C., whereupon allyl bromide (0.58 mL, 6.6 mmol) was added. The reaction was allowed to warm to rt, where it was stirred for 2 h. The reaction was quenched with 10% Rochelle's salt, then diluted with MTBE. The organic layer was separated, and the aqueous was extracted twice more with MTBE. The combined organic extracts were washed with 10% Rochelle's salt, saturated NH$_4$Cl (2×), H$_2$O, saturated NaHCO$_3$, and brine. After drying over MgSO$_4$, the concentrated mixture was chromatographed on silica gel (5:1 hexanes/EtOAc), yielding 17.

EXAMPLE 22

Example of Palladium Coupling of Homoenolate with Acid Halide

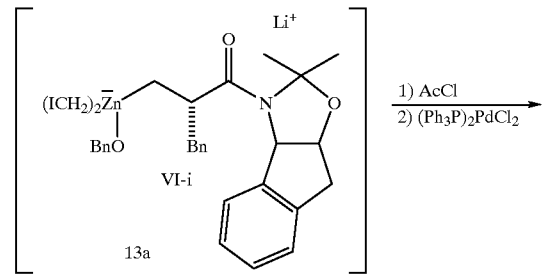

27
-continued

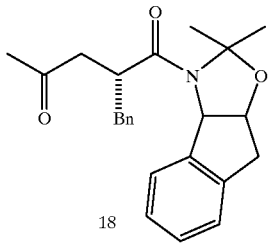

18

To a 0.090 M solution of zinc homoenolate 13a (15 mL, 1.32 mmol) was added acetyl chloride (0.47 mL, 6.6 mmol) at T$_i$ 10° C. After cooling to 0° C., bis(triphenylphosphine) palladium dichloride (47 mg, 6.7×10$^{-2}$ mmol) was added. The solution was stirred for 1 h at 0° C., then overnight at rt. HPLC assay indicated 80 area % conversion of 13a, providing 18. The reaction was quenched with saturated NaHCO$_3$ and 10% Rochelle's salt. After diluting with H$_2$O, the mixture was extracted with MTBE (2×). The combined organic extracts were washed with 10% Rochelle's salt, saturated NaHCO$_3$, and brine, then dried over MgSO$_4$. Concentration yielded crude 18.

EXAMPLE 23

Example of Palladium Coupling of Homoenolate with Aryl Iodide

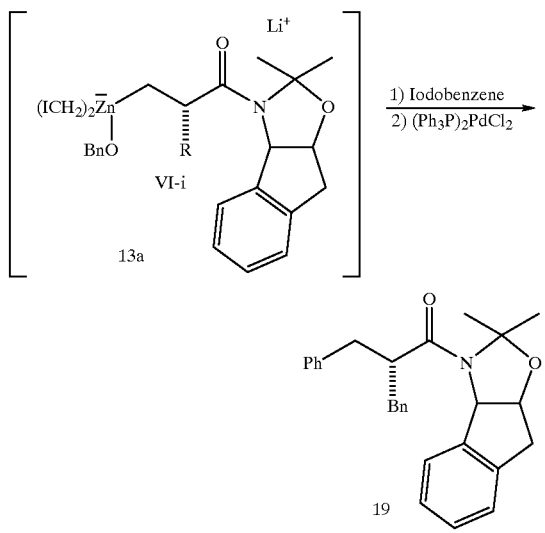

To a 0.090 M solution of zinc homoenolate 13a (15 mL, 1.32 mmol) at 0° C. was added iodobenzene (0.30 mL, 6.6 mmol), followed by bis(triphenylphosphine)palladium dichloride (47 mg, 6.7×10$^{-2}$ mmol). The solution was stirred for 1 h at 0° C., then overnight at rt (room temperature). HPLC assay indicated 98 area % conversion of 13a, providing 19. The reaction was quenched with saturated NaHCO$_3$ and 10% Rochelle's salt. After diluting with H$_2$O, the mixture was extracted with MTBE (2×). The combined organic extracts were washed with 10% Rochelle's salt, saturated NaHCO$_3$, and brine, then dried over MgSO$_4$. Concentration yielded crude 19.

28
EXAMPLE 24

Example of Palladium Coupling of Homoenolate with Aryl Triflate

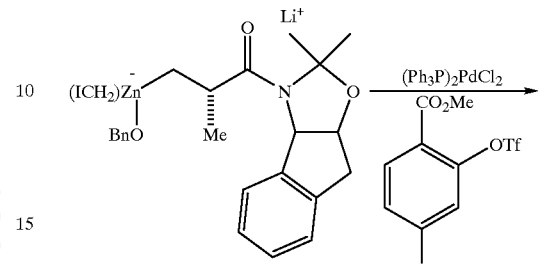

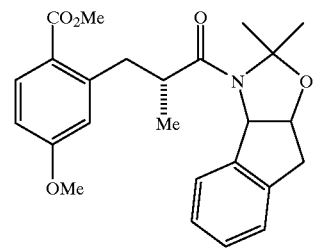

To a solution of zinc homoenolate 14a (3.5 mmol) at −78° C. was added acetyl chloride (1.0 mL, 14.6 mmol). The mixture was stirred 10 min, then allowed to warm to rt, where it stirred for 30 min. To this solution was added the triflate 20 (897 mg, 3.18 mmol) in THF (3 mL), followed by bis(triphenylphosphine)palladium dichloride (112 mg, 0.16 mmol). The mixture was heated to 55° C. and stirred overnight. The reaction was then cooled to rt and diluted with MTBE. This mixture was washed with H$_2$O, saturated NaHCO$_3$ and brine. The organic layer was then dried over MgSO$_4$ and concentrated. The crude product was chromatographed on silica gel (1:3 EtOAc/hexanes), yielding 21.

While the invention has been described and illustrated with reference to certain particular embodiments thereof, those skilled in the art will appreciate that various changes, modifications and substitutions can be made therein without departing from the spirit and scope of the invention. It is intended, therefore, that the invention be defined by the scope of the claims which follow and that such claims be interpreted as broadly as is reasonable.

What is claimed is:

1. A process for making a compound of formula VI

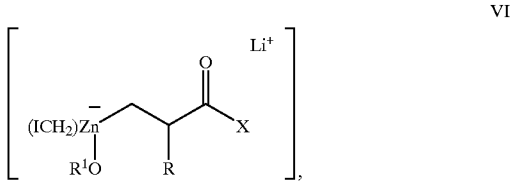

VI comprising treating IV

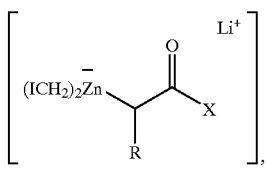

with an alkoxy lithium reagent in an aprotic solvent in an inert atmosphere at a temperature from −50° C. to −80° C., wherein:

R is any moiety capable of bonding to the alpha-carbon; the alkoxy lithium reagent is selected from an alkyl-OLi, a benzyl-OLi and a lithium dialkoxide reagent;

$R^1$—O— is the alkoxy derived from the alkoxy lithium reagent; and

X is a di-substituted amino group which is capable of forming an N,N-disubstituted amide with the carbonyl group to which it is attached.

2. The process of claim 1 wherein:

R is selected from —$C_{1-10}$ alkyl, phenyl, benzyl, heterocycle, —$C_{1-10}$ alkenyl, —$C_{1-10}$ alkyl-O—$C_{1-10}$ alkyl, —$C_{1-10}$ alkoxy, and —$NR^3R^4$ wherein each of $R^3$ and $R^4$ are independently selected from —H, —$C_{1-10}$ alkyl, phenyl, benzyl, —$C_{1-10}$ alkenyl and heterocycle;

the alkoxy lithium reagent is selected from $R^1$—OLi and $R^1(OLi)_2$, wherein $R^1$ is selected from: $C_{1-10}$ alkyl, $C_{1-10}$ alkenyl, phenyl, benzyl and heterocycle; and X is —$NR^7R^8$, wherein a) $R^7$ and $R^8$ are independently selected from —$C_{1-10}$ alkyl, —$C_{1-10}$ alkyl-O—$C_{1-10}$ alkyl, —$C_{1-10}$ alkyl-$C_{1-10}$ alkenyl, phenyl, benzyl, heterocycle, and —C(O)O—$R^9$, wherein $R^9$ is selected from —$C_{1-10}$ alkyl, —$C_{1-10}$ alkyl-O—$C_{1-10}$ alkyl, —$C_{2-10}$ alkyl-$C_{1-10}$ alkenyl, phenyl, benzyl, and heterocycle;

b) $R^7$ and $R^8$ together are —$(CH_2)_n$— wherein n is an integer selected form 2 to 5, so that $R^7$ and $R^8$ are joined together with the nitrogen to which they are attached to form cyclic structure of formula

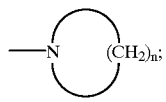

c) $R^7$ and $R^8$ together with the nitrogen to which they are attached are joined to form an oxazolidinone of formula

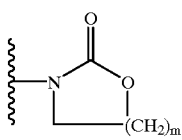

wherein m is an integer selected from 1 and 2, or d) $R^7$ and $R^8$ together with the nitrogen to which they are attached form a chiral auxiliary represented as "Xc.".

3. The process of claim 2 wherein R is selected from methyl and benzyl.

4. The process of claim 3 wherein R is benzyl.

5. The process of claim 2 wherein the alkoxy lithium reagent is selected from ethyl-OLi, n-propyl-OLi, lithium benzylalkoxide, $LiO(CH_2)_2OLi$ and $LiO(CH_2)_3OLi$.

6. The The process of claim 5 wherein the alkoxy lithium reagent is lithium benzylalkoxide.

7. The process of claim 1 wherein X is a chiral auxiliary represented as Xc, the compound of formula VI has the formula VI-i

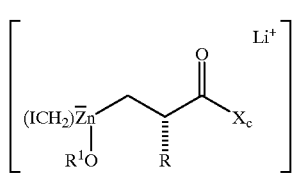

and the compound of formula IV has the formula IV-i

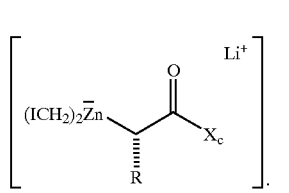

8. The process of claim 7 wherein Xc is selected from:

i)

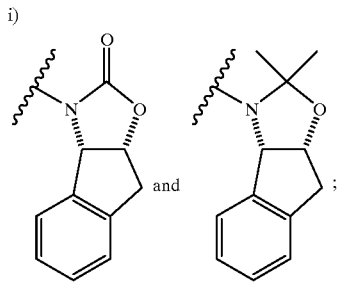

ii)

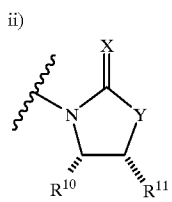

wherein

X is selected from O and S,

Y is selected from O, —N($C_{1-10}$ alkyl)—, and S, $R^{10}$ is selected from —$C_{1-10}$ alkyl, —C(O)—$C_{1-10}$ alkyl, benzyl, —COO—$C_{1-10}$ alkyl and aryl, and $R^{11}$ is selected from $-C_{1-10}$ alkyl and aryl;

iii)

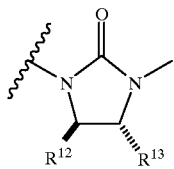

wherein $R^{12}$ and $R^{13}$ are both the same and are selected from $C_{1-10}$ alkyl and aryl, or $R^{12}$ and $R^{13}$ are joined together as $-(CH_2)_4-$;

iv)

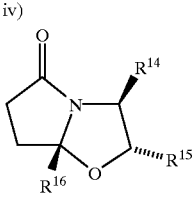

wherein $R^{14}$ is $C_{1-10}$ alkyl, $R^{15}$ is aryl, and $R^{16}$ is selected from $C_{1-10}$ alkyl and H;

v)

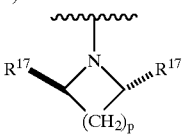

wherein $R^{17}$ is an alkyl ether, and p is an integer selected from 0, 2 and 3;

vi)

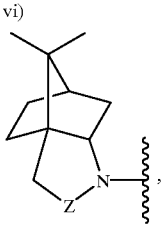

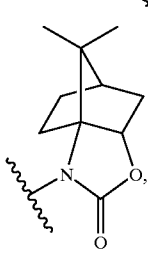

-continued

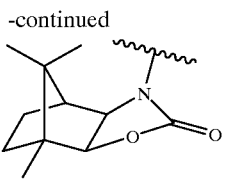

wherein Z is selected from O and $SO_2$; and vii) a)

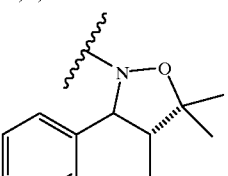

b)

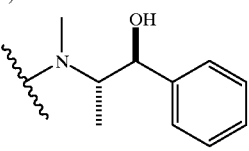

c)

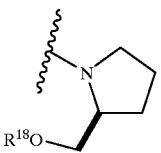

wherein $R^{18}$ is selected from H, $C_{1-10}$ alkyl, and silyl, and d)

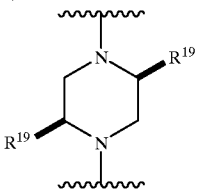

wherein $R^{19}$ is selected from $C_{1-10}$ alkyl and benzyl.

9. The process of claim 8 wherein Xc is

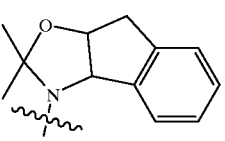

10. The process of claim 1 further comprising the step of adding II

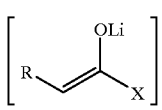

II to at least 0.5 equivalents of $(ICH_2)_2Zn$ to form the compound of formula IV.

11. The process of claim 10 further comprising the step of adding alkyl lithium to

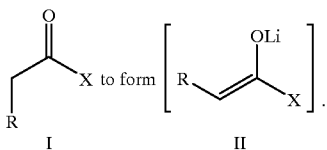

12. A process for making a zincate homoenolate comprising the step of treating a compound of formula IV

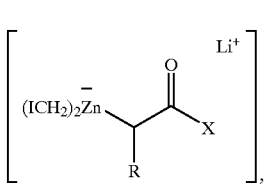

with an alkoxy lithium reagent in an aprotic solvent in an inert atmosphere at a temperature from −50° C. to −80° C. wherein:
  R is any moiety capable of bonding to the alpha-carbon;
  the alkoxy lithium reagent is selected from an alkyl-OLi, a benzyl-OLi and a lithium dialkoxide reagent; and
  X is a di-substituted amino group which is capable of forming an N,N-disubstituted amide with the carbonyl group to which it is attached.

13. The process of claim 12 wherein the compound of formula IV has the formula IV-i

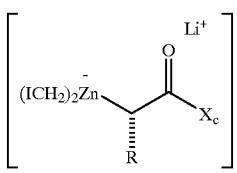

wherein Xc is a di-substituted amino group which is a chiral auxiliary.

14. The process of claim 13 further comprising the steps of
  (i) treating the zincate homoenolate produced by the process of claim 13 with $R^{20}$—Y and $(Ph_3P)_2PdCl_2$ to form IX-i

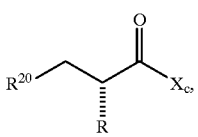

wherein $R^{20}$ is selected from $C_{1-10}$ alkyl, $C_{1-10}$ alkenyl, aryl and $C_{1-10}$ alkyl-C(O)—, and
  Y is selected from halo and $-OSO_2CF_3$, provided that when $R^{20}$ is $C_{1-10}$ alkyl-C(O)—, Y is halo, and
  (ii) isolating the compound of formula IX-i.

15. The process of claim 13 further comprising the steps of
  (i) treating the zincate homoenolate produced by the process of claim 13 with CuCN and $R^{21}Y'$ to form X-i

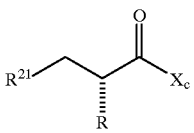

wherein $R^{21}$ is selected from $C_{1-10}$ alkyl and $C_{1-10}$ alkenyl, and Y' is halo, and
  (ii) isolating the compound of formula X-i.

16. A process for making a compound of formula VII

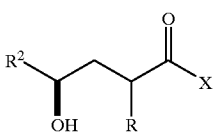

comprising the steps of:
  (a) treating a compound of formula IV

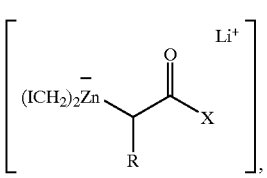

with an alkoxy lithium reagent in an aprotic solvent in an inert atmosphere at a temperature from −50° C. to −80° C. to form a compound of formula VI

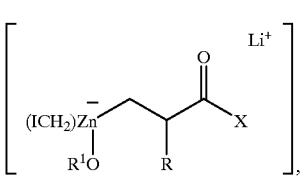

wherein:
  R is any moiety capable of bonding to the alpha-carbon;
  the alkoxy lithium reagent is selected from an alkyl-OLi, a benzyl-OLi and a lithium dialkoxide reagent;
  $R^1$—O— is the alkoxy derived from the alkoxy lithium reagent; and
  X is a di-substituted amino group which is capable of forming an N,N-disubstituted amide with the carbonyl group to which it is attached;
  (b) treating the compound of formula VI with a titanium transmetallation reagent selected from $Cl_3Ti(O-isopropyl)$, $TiCl(O-isopropyl)_3$, $TiCl_2(O-isopropyl)_2$, and $TiCl_4$; and
  (c) adding an aldehyde of formula $R^2CHO$ to the product of step (b) to form the compound VII, wherein $R^2CHO$ is an alpha amino aldehyde derived from an amino acid; and $R^2$ is the radical derived from $R^2CHO$.

17. The process of claim 16 wherein the titanium transmetallation reagent is $Cl_3Ti(O-isopropyl)$.

18. The process of claim 16 wherein $R^2CHO$ is selected from

N-t-butoxylcarbonyl-L-phenylalaninal,
N-t-butoxylcarbonyl-L-alaninal,
N-t-butoxylcarbonyl-L-leucinal,
N-t-butoxylcarbonyl-O-benzyl-L-tyrosinal,
N-t-butoxylcarbonylO-methyl-L-tyrosinal,
N-t-butoxylcarbonyl-L-valinal, and
t-butyl (S)-4-formyl-2,2-dimethyl-3-oxazolidinecarboxylate.

19. The process of claim 16 wherein X is a chiral auxiliary represented as Xc, and the product VII has the formula VII-i

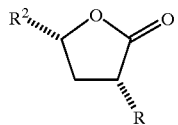

VII-i

20. The process of claim 19 wherein R is benzyl and Xc is cis-aminoindanol.

21. A process for making a compound of formula VIII-i

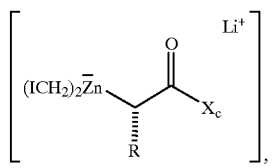

VIII-i comprising the steps of:

(a) treating a compound of formula IV-i

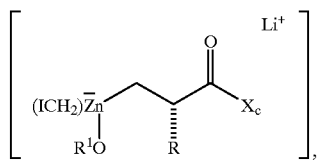

IV-i with an alkoxy lithium reagent in an aprotic solvent in an inert atmosphere at a temperature from −50° C. to −80° C. to form a compound of formula VI-i

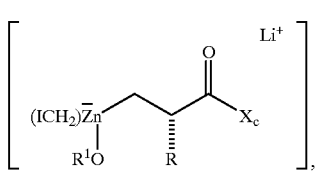

VI-i (b) treating the compound of formula VI-i with a titanium transmetallation reagent selected from Cl$_3$Ti(O-isopropyl), TiCl(O-isopropyl)$_3$, TiCl$_2$(O-isopropyl)$_2$, and TiCl$_4$;

(c) adding an aldehyde of formula R$^2$CHO to the product of step (b) to form a compound of formula VII-i; and

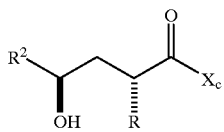

VII-i (d) adding p-toluenesulfonic acid to the compound of formula VII-i to form the compound VIII-i;

wherein:
R is any moiety capable of bonding to the alpha-carbon;
the alkoxy lithium reagent is selected from an alkyl-OLi, a benzyl-OLi and a lithium dialkoxide reagent;
R$^1$—O— is the alkoxy derived from the alkoxy lithium reagent;
R$^2$CHO is an alpha amino aldehyde derived from an amino acid;
R$^2$ is the radical derived from R$^2$CHO; and
Xc is a chiral auxiliary which is a di-substituted amino group capable of forming an N,N-disubstituted amide with the carbonyl group to which it is attached.

22. A process for making a compound of formula IX-i

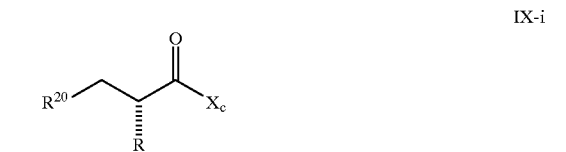

IX-i comprising the steps of:

(a) treating a compound of formula IV-i

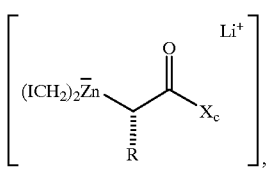

IV-i with an alkoxy lithium reagent in an aprotic solvent in an inert atmosphere at a temperature from −50° C. to −80° C. to form a compound of formula VI-i

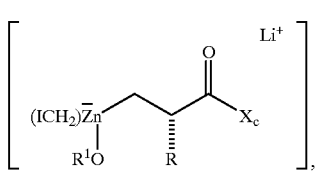

VI-i wherein:
R is any moiety capable of bonding to the alpha-carbon;
the alkoxy lithium reagent is selected from an alkyl-OLi, a benzyl-OLi and a lithium dialkoxide reagent;
R$^1$—O— is the alkoxy derived from the alkoxy lithium reagent; and
Xc is a chiral auxiliary which is a di-substituted amino group capable of forming an N,N-disubstituted amide with the carbonyl group to which it is attached; and (b) treating the compound of formula VI-i with $R^{20}$—Y and $(Ph_3P)_2PdCl_2$ to form the compound IX-i, wherein $R^{20}$ is selected from $C_{1-10}$ alkyl, $C_{1-10}$ alkenyl, aryl and $C_{1-10}$ alkyl-C(O)—, and Y is selected from halo and —$OSO_2CF_3$, provided that when $R^{20}$ is $C_{1-10}$ alkyl-C(O)—, Y is halo.

23. A process for making a compound of formula X-i

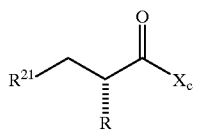

X-i comprising the steps of:
(a) treating a compound of formula IV-i

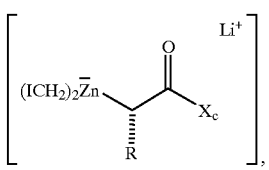

IV-i with an alkoxy lithium reagent in an aprotic solvent in an inert atmosphere at a temperature from –50° C. to –80° C. to form a compound of formula VI-i

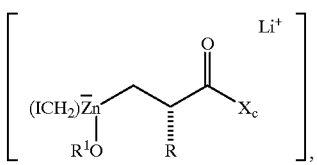

VI-i wherein:
R is any moiety capable of bonding to the alpha-carbon;

the alkoxy lithium reagent is selected from an alkyl-OLi, a benzyl-OLi and a lithium dialkoxide reagent;

$R^1$—O— is the alkoxy derived from the alkoxy lithium reagent; and

Xc is a chiral auxiliary which is a di-substituted amino group capable of forming an N,N-disubstituted amide with the carbonyl group to which it is attached; and (b) treating the compound of formula VI-i with CuCN and $R^{21}$Y' to form the compound X-i, wherein $R^{21}$ is selected from $C_{1-10}$ alkyl and $C_{1-10}$ alkenyl, and Y' is halo.

24. The process of claim 16 wherein $R^2CHO$ is selected from:

N-t-butoxylcarbonyl-L-phenylalaninal, N-t-butoxylcarbonyl-L-alaninal,

N-t-butoxylcarbonyl-L-leucinal,

N-t-butoxylcarbonyl-O-benzyl-L-tyrosinal,

N-t-butoxylcarbonylO-methyl-L-tyrosinal,

N-t-butoxylcarbonyl-L-valinal, and t-butyl (S)-4-formyl-2,2-dimethyl-3-oxazolidinecarboxylate.

25. The process of claim 21 wherein $R^2CHO$ is selected from:

N-t-butoxylcarbonyl-L-phenylalaninal, N-t-butoxylcarbonyl-L-alaninal,

N-t-butoxylcarbonyl-L-leucinal,

N-t-butoxylcarbonyl-O-benzyl-L-tyrosinal,

N-t-butoxylcarbonylO-methyl-L-tyrosinal,

N-t-butoxylcarbonyl-L-valinal, and t-butyl (S)-4-formyl-2,2-dimethyl-3-oxazolidinecarboxylate.

* * * * *